(12) United States Patent
de Villiers et al.

(10) Patent No.: US 9,827,108 B2
(45) Date of Patent: Nov. 28, 2017

(54) CUSTOMIZED INTERVERTEBRAL PROSTHETIC DISC WITH SHOCK ABSORPTION

(71) Applicant: Simplify Medical Pty Ltd., Paddington NSW (AU)

(72) Inventors: Malan de Villiers, Wapadrand (ZA); David Hovda, Mountain View, CA (US); James Shapiro, San Francisco, CA (US)

(73) Assignee: Simplify Medical Pty Ltd, Paddington, NSW (AU)

( * ) Notice: Subject to any disclaimer, the term of this patent is extended or adjusted under 35 U.S.C. 154(b) by 0 days.

(21) Appl. No.: 15/606,587

(22) Filed: May 26, 2017

(65) Prior Publication Data
US 2017/0258602 A1    Sep. 14, 2017

Related U.S. Application Data

(60) Continuation of application No. 15/368,437, filed on Dec. 2, 2016, now Pat. No. 9,687,355, which is a
(Continued)

(51) Int. Cl.
| A61F 2/44 | (2006.01) |
| A61F 2/46 | (2006.01) |
| A61F 2/30 | (2006.01) |

(52) U.S. Cl.
CPC ............ *A61F 2/4425* (2013.01); *A61F 2/442* (2013.01); *A61F 2/4611* (2013.01);
(Continued)

(58) Field of Classification Search
CPC ........ A61F 2/442; A61F 2/4611; A61F 2/447; A61F 2/4455
See application file for complete search history.

(56) References Cited

U.S. PATENT DOCUMENTS

| 3,486,505 A | 12/1969 | Gordon |
| 3,867,728 A | 2/1975 | Stubstad et al. |

(Continued)

FOREIGN PATENT DOCUMENTS

| DE | 3023353 A1 | 4/1981 |
| DE | 10035182 A1 | 2/2002 |

(Continued)

OTHER PUBLICATIONS

Buttner-Janz, The Development of the Artificial Disc. Introduction, pp. 1-18, Library of Congress Catalogue No. 92-75582, ISBN 0-9635430-0-8 (1989).

(Continued)

*Primary Examiner* — Christian Sevilla
(74) *Attorney, Agent, or Firm* — Wilson Sonsini Goodrich & Rosati

(57) ABSTRACT

A prosthesis system comprises plates that can be positioned against vertebrae and a selected resilient core that can be positioned between the plates to allow the plates to articulate. The selected resilient core can be chosen from a plurality of cores in response to patient characteristics, such as age and/or intervertebral mobility, such that the prosthesis implanted in the patient is tailored to the needs of the patient. The plurality of cores may comprise cores with different resiliencies, and one of the cores can be selected such that the upper and lower plates articulate with the desired shock absorbing resiliency and/or maximum angle of inclination when the one selected core is positioned between the plates.

7 Claims, 10 Drawing Sheets

Related U.S. Application Data continuation of application No. 13/941,121, filed on Jul. 12, 2013, now Pat. No. 9,554,917, which is a division of application No. 12/883,068, filed on Sep. 15, 2010, now Pat. No. 8,506,631, which is a division of application No. 11/836,684, filed on Aug. 9, 2007, now abandoned.

(52) U.S. Cl.
CPC .. *A61F 2002/305* (2013.01); *A61F 2002/3071* (2013.01); *A61F 2002/30383* (2013.01); *A61F 2002/30405* (2013.01); *A61F 2002/30495* (2013.01); *A61F 2002/30563* (2013.01); *A61F 2002/30568* (2013.01); *A61F 2002/30579* (2013.01); *A61F 2002/30601* (2013.01); *A61F 2002/30616* (2013.01); *A61F 2002/30617* (2013.01); *A61F 2002/30662* (2013.01); *A61F 2002/30663* (2013.01); *A61F 2002/30673* (2013.01); *A61F 2002/30841* (2013.01); *A61F 2002/30884* (2013.01); *A61F 2002/30899* (2013.01); *A61F 2002/30904* (2013.01); *A61F 2002/443* (2013.01); *A61F 2002/4628* (2013.01); *A61F 2220/0025* (2013.01); *A61F 2250/0085* (2013.01); *A61F 2250/0097* (2013.01); *A61F 2310/00017* (2013.01); *A61F 2310/00023* (2013.01); *A61F 2310/00029* (2013.01); *A61F 2310/00179* (2013.01); *A61F 2310/00407* (2013.01)

(56) References Cited

U.S. PATENT DOCUMENTS

| | | | |
|---|---|---|---|
| 4,309,777 A | 1/1982 | Patil | |
| 4,531,917 A | 7/1985 | Linkow et al. | |
| 4,566,466 A | 1/1986 | Ripple et al. | |
| 4,619,660 A | 10/1986 | Christiansen et al. | |
| 4,673,407 A | 6/1987 | Martin | |
| 4,759,766 A | 7/1988 | Buettner-Janz et al. | |
| 4,759,769 A | 7/1988 | Hedman et al. | |
| 4,834,757 A | 5/1989 | Brantigan | |
| 4,863,477 A | 9/1989 | Monson | |
| 4,904,261 A | 2/1990 | Dove et al. | |
| 4,917,704 A | 4/1990 | Frey et al. | |
| 4,932,969 A | 6/1990 | Frey et al. | |
| 4,946,378 A | 8/1990 | Hirayama et al. | |
| 4,997,432 A | 3/1991 | Keller | |
| 5,035,716 A | 7/1991 | Downey | |
| 5,057,108 A | 10/1991 | Shetty et al. | |
| 5,071,437 A | 12/1991 | Steffee | |
| 5,122,130 A | 6/1992 | Keller | |
| 5,195,526 A | 3/1993 | Michelson | |
| 5,258,031 A | 11/1993 | Salib et al. | |
| 5,282,661 A | 2/1994 | Arnberger | |
| 5,306,308 A | 4/1994 | Gross et al. | |
| 5,314,477 A | 5/1994 | Marnay | |
| 5,320,644 A | 6/1994 | Baumgartner | |
| 5,370,697 A | 12/1994 | Baumgartner | |
| 5,394,457 A | 2/1995 | Leibinger et al. | |
| 5,401,269 A | 3/1995 | Buettner-Janz et al. | |
| 5,415,704 A | 5/1995 | Davidson | |
| 5,458,642 A | 10/1995 | Beer et al. | |
| 5,462,575 A | 10/1995 | Del Corso | |
| 5,484,437 A | 1/1996 | Michelson | |
| 5,489,307 A | 2/1996 | Kuslich et al. | |
| 5,505,732 A | 4/1996 | Michelson | |
| 5,507,816 A | 4/1996 | Bullivant | |
| 5,534,030 A | 7/1996 | Navarro et al. | |
| 5,556,431 A | 9/1996 | Büttner-Janz | |
| 5,665,122 A * | 9/1997 | Kambin | A61F 2/4455 411/55 |
| 5,674,296 A | 10/1997 | Bryan et al. | |
| 5,676,701 A | 10/1997 | Yuan et al. | |
| 5,676,702 A | 10/1997 | Ratron | |
| 5,683,465 A | 11/1997 | Shinn et al. | |
| 5,702,450 A | 12/1997 | Bisserie | |
| 5,709,683 A | 1/1998 | Bagby | |
| 5,728,159 A | 3/1998 | Stroever et al. | |
| 5,741,253 A | 4/1998 | Michelson | |
| 5,776,198 A | 7/1998 | Rabbe et al. | |
| 5,782,832 A | 7/1998 | Larsen et al. | |
| 5,797,909 A | 8/1998 | Michelson | |
| 5,824,094 A | 10/1998 | Serhan et al. | |
| 5,836,948 A | 11/1998 | Zucherman et al. | |
| 5,865,846 A | 2/1999 | Bryan et al. | |
| 5,865,848 A | 2/1999 | Baker | |
| 5,888,226 A | 3/1999 | Rogozinski | |
| 5,895,428 A | 4/1999 | Berry | |
| 5,899,901 A | 5/1999 | Middleton | |
| 5,899,911 A | 5/1999 | Carter | |
| 5,928,284 A | 7/1999 | Mehdizadeh | |
| 5,989,251 A | 11/1999 | Nichols | |
| 5,989,291 A | 11/1999 | Ralph et al. | |
| 6,001,130 A | 12/1999 | Bryan et al. | |
| 6,019,792 A | 2/2000 | Cauthen | |
| 6,022,376 A | 2/2000 | Assell et al. | |
| 6,039,761 A | 3/2000 | Li et al. | |
| 6,039,763 A | 3/2000 | Shelokov | |
| 6,080,155 A | 6/2000 | Michelson | |
| 6,083,228 A | 7/2000 | Michelson | |
| 6,086,613 A | 7/2000 | Camino et al. | |
| 6,096,038 A | 8/2000 | Michelson | |
| 6,102,950 A * | 8/2000 | Vaccaro | A61F 2/447 606/247 |
| 6,132,465 A | 10/2000 | Ray et al. | |
| 6,136,031 A | 10/2000 | Middleton | |
| 6,139,551 A | 10/2000 | Michelson et al. | |
| 6,139,579 A | 10/2000 | Steffee et al. | |
| 6,143,033 A | 11/2000 | Paul et al. | |
| 6,146,421 A | 11/2000 | Gordon et al. | |
| 6,156,067 A | 12/2000 | Bryan et al. | |
| 6,159,214 A | 12/2000 | Michelson | |
| 6,162,252 A | 12/2000 | Kuras et al. | |
| 6,174,311 B1 | 1/2001 | Branch et al. | |
| 6,176,881 B1 | 1/2001 | Schaer et al. | |
| 6,193,757 B1 | 2/2001 | Foley et al. | |
| 6,224,595 B1 | 5/2001 | Michelson | |
| 6,224,607 B1 | 5/2001 | Michelson | |
| 6,231,609 B1 | 5/2001 | Mehdizadeh | |
| 6,235,030 B1 | 5/2001 | Zucherman et al. | |
| 6,261,296 B1 | 7/2001 | Aebi et al. | |
| 6,264,695 B1 | 7/2001 | Stoy | |
| 6,290,726 B1 | 9/2001 | Pope et al. | |
| 6,296,664 B1 | 10/2001 | Middleton | |
| 6,315,797 B1 | 11/2001 | Middleton | |
| 6,322,567 B1 | 11/2001 | Mittelstadt et al. | |
| 6,336,941 B1 | 1/2002 | Subba et al. | |
| 6,348,071 B1 | 2/2002 | Steffee et al. | |
| 6,368,350 B1 | 4/2002 | Erickson et al. | |
| 6,368,351 B1 | 4/2002 | Glenn et al. | |
| 6,375,681 B1 | 4/2002 | Truscott | |
| 6,375,682 B1 | 4/2002 | Fleischmann et al. | |
| 6,395,032 B1 | 5/2002 | Gauchet | |
| 6,402,785 B1 | 6/2002 | Zdeblick et al. | |
| 6,409,766 B1 | 6/2002 | Brett | |
| 6,413,278 B1 | 7/2002 | Marchosky | |
| 6,416,551 B1 | 7/2002 | Keller | |
| 6,436,098 B1 | 8/2002 | Michelson | |
| 6,440,139 B2 | 8/2002 | Michelson | |
| 6,447,544 B1 | 9/2002 | Michelson | |
| 6,478,800 B1 | 11/2002 | Fraser et al. | |
| 6,517,544 B1 | 2/2003 | Michelson | |
| 6,517,580 B1 | 2/2003 | Ramadan et al. | |
| 6,520,967 B1 | 2/2003 | Cauthen | |
| 6,520,996 B1 | 2/2003 | Manasas et al. | |
| 6,527,804 B1 | 3/2003 | Gauchet et al. | |
| 6,533,817 B1 | 3/2003 | Norton et al. | |
| 6,537,279 B1 | 3/2003 | Michelson | |
| 6,554,863 B2 | 4/2003 | Paul et al. | |
| 6,562,047 B2 | 5/2003 | Ralph et al. | |
| 6,562,074 B2 | 5/2003 | Gerbec et al. | |

(56) References Cited

U.S. PATENT DOCUMENTS

| | | |
|---|---|---|
| 6,565,574 B2 | 5/2003 | Michelson |
| 6,582,466 B1 | 6/2003 | Gauchet |
| 6,582,468 B1 | 6/2003 | Gauchet |
| 6,592,624 B1 | 7/2003 | Fraser et al. |
| 6,599,294 B2 | 7/2003 | Fuss et al. |
| 6,607,558 B2 | 8/2003 | Kuras |
| 6,607,559 B2 | 8/2003 | Ralph et al. |
| 6,610,092 B2 | 8/2003 | Ralph et al. |
| 6,623,525 B2 | 9/2003 | Ralph et al. |
| 6,645,248 B2 | 11/2003 | Casutt |
| 6,648,895 B2 | 11/2003 | Burkus et al. |
| 6,652,533 B2 | 11/2003 | O'Neil |
| 6,660,038 B2 | 12/2003 | Boyer et al. |
| 6,666,866 B2 | 12/2003 | Martz et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,682,562 B2 | 1/2004 | Viart et al. |
| 6,689,132 B2 | 2/2004 | Biscup |
| 6,706,068 B2 | 3/2004 | Ferree |
| 6,709,439 B2 | 3/2004 | Rogers et al. |
| 6,712,819 B2 | 3/2004 | Zucherman et al. |
| 6,712,825 B2 | 3/2004 | Aebi et al. |
| 6,719,794 B2 | 4/2004 | Gerber et al. |
| 6,723,097 B2 | 4/2004 | Fraser et al. |
| 6,726,720 B2 | 4/2004 | Ross et al. |
| 6,726,721 B2 | 4/2004 | Stoy et al. |
| 6,733,532 B1 | 5/2004 | Gauchet et al. |
| 6,740,118 B2 | 5/2004 | Eisermann et al. |
| 6,740,119 B2 | 5/2004 | Ralph et al. |
| 6,752,832 B2 | 6/2004 | Neumann |
| 6,755,841 B2 | 6/2004 | Fraser et al. |
| 6,764,512 B2 | 7/2004 | Keller |
| 6,764,515 B2 | 7/2004 | Ralph et al. |
| 6,770,095 B2 | 8/2004 | Grinberg et al. |
| 6,790,233 B2 | 9/2004 | Brodke et al. |
| 6,793,678 B2 | 9/2004 | Hawkins |
| 6,814,737 B2 | 11/2004 | Cauthen |
| 6,821,298 B1 | 11/2004 | Jackson |
| 6,827,740 B1 | 12/2004 | Michelson |
| 6,830,570 B1 | 12/2004 | Frey et al. |
| 6,846,328 B2 | 1/2005 | Cauthen |
| 6,852,126 B2 | 2/2005 | Ahlgren |
| 6,863,673 B2 | 3/2005 | Gerbec et al. |
| 6,875,213 B2 | 4/2005 | Michelson |
| 6,896,680 B2 | 5/2005 | Michelson |
| 6,899,735 B2 | 5/2005 | Coates et al. |
| 6,936,071 B1 | 8/2005 | Marnay et al. |
| 6,936,132 B2 | 8/2005 | Topolnitsky |
| 6,964,686 B2 | 11/2005 | Gordon |
| 6,966,929 B2 | 11/2005 | Mitchell |
| 6,966,931 B2 | 11/2005 | Huang |
| 6,986,788 B2 | 1/2006 | Paul et al. |
| 6,989,011 B2 | 1/2006 | Paul et al. |
| 6,994,727 B2 | 2/2006 | Khandkar et al. |
| 7,011,684 B2 | 3/2006 | Eckman |
| 7,022,138 B2 | 4/2006 | Mashburn |
| 7,025,787 B2 | 4/2006 | Bryan et al. |
| 7,044,983 B1 | 5/2006 | Cheng |
| 7,056,344 B2 | 6/2006 | Huppert et al. |
| 7,060,073 B2 | 6/2006 | Frey et al. |
| 7,066,958 B2 | 6/2006 | Ferree |
| 7,081,120 B2 | 7/2006 | Li et al. |
| 7,083,651 B2 | 8/2006 | Diaz et al. |
| 7,087,055 B2 | 8/2006 | Lim et al. |
| 7,097,648 B1 | 8/2006 | Globerman et al. |
| 7,115,132 B2 | 10/2006 | Errico et al. |
| 7,118,580 B1 | 10/2006 | Beyersdorff et al. |
| 7,147,665 B1 | 12/2006 | Bryan et al. |
| 7,153,325 B2 | 12/2006 | Kim et al. |
| 7,169,182 B2 | 1/2007 | Errico et al. |
| 7,179,294 B2 | 2/2007 | Eisermann et al. |
| 7,182,784 B2 | 2/2007 | Evans et al. |
| 7,198,644 B2 | 4/2007 | Schultz et al. |
| 7,207,991 B2 | 4/2007 | Michelson |
| 7,214,244 B2 | 5/2007 | Zubok et al. |
| 7,217,291 B2 | 5/2007 | Zucherman et al. |
| 7,235,082 B2 | 6/2007 | Bartish et al. |
| 7,235,103 B2 | 6/2007 | Rivin |
| 7,250,060 B2 | 7/2007 | Trieu |
| 7,255,714 B2 | 8/2007 | Malek |
| 7,261,739 B2 | 8/2007 | Ralph et al. |
| 7,267,688 B2 | 9/2007 | Ferree |
| 7,270,679 B2 | 9/2007 | Istephanous et al. |
| 7,270,682 B2 | 9/2007 | Frigg et al. |
| 7,303,582 B2 | 12/2007 | Brady et al. |
| 7,303,583 B1 | 12/2007 | Schaer et al. |
| 7,318,839 B2 | 1/2008 | Malberg et al. |
| 7,326,250 B2 | 2/2008 | Beaurain et al. |
| 7,331,995 B2 | 2/2008 | Eisermann et al. |
| 7,429,270 B2 | 9/2008 | Baumgartner et al. |
| 7,442,211 B2 | 10/2008 | De et al. |
| 7,452,380 B2 | 11/2008 | Zubok et al. |
| 7,491,241 B2 | 2/2009 | Errico et al. |
| 7,494,508 B2 | 2/2009 | Zeegers et al. |
| 7,517,363 B2 | 4/2009 | Rogers et al. |
| 7,549,995 B2 | 6/2009 | Schultz |
| 7,563,286 B2 | 7/2009 | Gerber et al. |
| 7,601,174 B2 | 10/2009 | Kelly et al. |
| 7,708,776 B1 | 5/2010 | Blain et al. |
| 7,731,753 B2 | 6/2010 | Reo et al. |
| 7,909,876 B2 | 3/2011 | Dooris et al. |
| 8,038,715 B2 | 10/2011 | Kim et al. |
| 8,277,508 B2 | 10/2012 | Trieu |
| 8,388,681 B2 | 3/2013 | Paul et al. |
| 8,506,631 B2 | 8/2013 | De et al. |
| 9,554,917 B2 | 1/2017 | De et al. |
| 9,687,355 B2 | 6/2017 | De et al. |
| 2001/0016773 A1 | 8/2001 | Serhan et al. |
| 2001/0029377 A1 | 10/2001 | Aebi et al. |
| 2002/0022845 A1 | 2/2002 | Zdeblick et al. |
| 2002/0035400 A1 | 3/2002 | Bryan et al. |
| 2002/0045904 A1 | 4/2002 | Fuss et al. |
| 2002/0068936 A1 | 6/2002 | Burkus et al. |
| 2002/0091392 A1 | 7/2002 | Michelson |
| 2002/0116009 A1 | 8/2002 | Fraser et al. |
| 2002/0123753 A1 | 9/2002 | Michelson |
| 2002/0128715 A1 | 9/2002 | Bryan et al. |
| 2002/0165550 A1 | 11/2002 | Frey et al. |
| 2002/0177897 A1 | 11/2002 | Michelson |
| 2002/0198532 A1 | 12/2002 | Michelson |
| 2003/0009224 A1 | 1/2003 | Kuras |
| 2003/0023245 A1 | 1/2003 | Ralph et al. |
| 2003/0028249 A1 | 2/2003 | Baccelli et al. |
| 2003/0040746 A1 | 2/2003 | Mitchell et al. |
| 2003/0045884 A1 | 3/2003 | Robie et al. |
| 2003/0045939 A1 | 3/2003 | Casutt |
| 2003/0074076 A1 | 4/2003 | Ferree et al. |
| 2003/0083747 A1 | 5/2003 | Winterbottom et al. |
| 2003/0100951 A1 | 5/2003 | Serhan et al. |
| 2003/0125739 A1 | 7/2003 | Bagga et al. |
| 2003/0130662 A1 | 7/2003 | Michelson |
| 2003/0135277 A1 | 7/2003 | Bryan et al. |
| 2003/0139812 A1 | 7/2003 | Garcia et al. |
| 2003/0187448 A1 | 10/2003 | Michelson |
| 2003/0191536 A1 | 10/2003 | Ferree |
| 2003/0195517 A1 | 10/2003 | Michelson |
| 2003/0195631 A1 | 10/2003 | Ferree |
| 2003/0199982 A1 | 10/2003 | Bryan |
| 2003/0204261 A1 | 10/2003 | Eisermann et al. |
| 2003/0208271 A1 | 11/2003 | Kuras |
| 2003/0229358 A1 | 12/2003 | Errico et al. |
| 2003/0233145 A1 | 12/2003 | Landry et al. |
| 2004/0002761 A1 | 1/2004 | Rogers et al. |
| 2004/0024407 A1 | 2/2004 | Ralph et al. |
| 2004/0024410 A1 | 2/2004 | Olson et al. |
| 2004/0030391 A1 | 2/2004 | Ferree |
| 2004/0034426 A1 | 2/2004 | Errico et al. |
| 2004/0054411 A1 | 3/2004 | Kelly et al. |
| 2004/0059318 A1 | 3/2004 | Zhang et al. |
| 2004/0073307 A1 | 4/2004 | Keller |
| 2004/0073311 A1 | 4/2004 | Ferree |
| 2004/0073312 A1 | 4/2004 | Eisermann et al. |
| 2004/0093087 A1 | 5/2004 | Ferree et al. |

(56) References Cited

U.S. PATENT DOCUMENTS

| | | |
|---|---|---|
| 2004/0097928 A1 | 5/2004 | Zdeblick et al. |
| 2004/0098131 A1 | 5/2004 | Bryan et al. |
| 2004/0117021 A1 | 6/2004 | Biedermann et al. |
| 2004/0143270 A1 | 7/2004 | Zucherman et al. |
| 2004/0143332 A1 | 7/2004 | Krueger et al. |
| 2004/0143334 A1 | 7/2004 | Ferree |
| 2004/0167626 A1 | 8/2004 | Geremakis et al. |
| 2004/0176843 A1 | 9/2004 | Zubok et al. |
| 2004/0186569 A1 | 9/2004 | Berry |
| 2004/0215342 A1 | 10/2004 | Suddaby |
| 2004/0225295 A1 | 11/2004 | Zubok et al. |
| 2004/0225365 A1 | 11/2004 | Eisermann et al. |
| 2004/0236426 A1 | 11/2004 | Ralph et al. |
| 2004/0243238 A1 | 12/2004 | Arnin et al. |
| 2004/0254644 A1 | 12/2004 | Taylor |
| 2005/0015094 A1 | 1/2005 | Keller |
| 2005/0015095 A1 | 1/2005 | Keller |
| 2005/0015152 A1 | 1/2005 | Sweeney |
| 2005/0021145 A1 | 1/2005 | De et al. |
| 2005/0021146 A1 | 1/2005 | De et al. |
| 2005/0027360 A1 | 2/2005 | Webb et al. |
| 2005/0038515 A1 | 2/2005 | Kunzler |
| 2005/0043800 A1 | 2/2005 | Paul et al. |
| 2005/0107881 A1 | 5/2005 | Alleyne et al. |
| 2005/0113842 A1 | 5/2005 | Bertagnoli et al. |
| 2005/0113928 A1 | 5/2005 | Cragg et al. |
| 2005/0143824 A1 | 6/2005 | Richelsoph et al. |
| 2005/0149189 A1 | 7/2005 | Mokhtar et al. |
| 2005/0154463 A1 | 7/2005 | Trieu |
| 2005/0165408 A1 | 7/2005 | Puno et al. |
| 2005/0171604 A1 | 8/2005 | Michalow |
| 2005/0192586 A1 | 9/2005 | Zucherman et al. |
| 2005/0192670 A1 | 9/2005 | Zubok et al. |
| 2005/0197702 A1 | 9/2005 | Coppes et al. |
| 2005/0197703 A1 | 9/2005 | Diaz et al. |
| 2005/0197706 A1 | 9/2005 | Hovorka et al. |
| 2005/0216081 A1 | 9/2005 | Taylor et al. |
| 2005/0216084 A1 | 9/2005 | Fleischmann et al. |
| 2005/0234553 A1 | 10/2005 | Gordon |
| 2005/0251260 A1 | 11/2005 | Gerber et al. |
| 2005/0251261 A1 | 11/2005 | Peterman |
| 2005/0251262 A1 | 11/2005 | De et al. |
| 2005/0261772 A1 | 11/2005 | Filippi et al. |
| 2005/0267580 A1 | 12/2005 | Suddaby |
| 2005/0267581 A1 | 12/2005 | Marnay et al. |
| 2006/0004377 A1 | 1/2006 | Keller |
| 2006/0004453 A1 | 1/2006 | Bartish, Jr. et al. |
| 2006/0015183 A1 | 1/2006 | Gilbert et al. |
| 2006/0020342 A1 | 1/2006 | Ferree et al. |
| 2006/0025862 A1 | 2/2006 | Villiers et al. |
| 2006/0029186 A1 | 2/2006 | De et al. |
| 2006/0030857 A1 | 2/2006 | De et al. |
| 2006/0030862 A1 | 2/2006 | De et al. |
| 2006/0036325 A1 | 2/2006 | Paul et al. |
| 2006/0041313 A1 | 2/2006 | Allard et al. |
| 2006/0041314 A1 | 2/2006 | Millard |
| 2006/0052870 A1 | 3/2006 | Ferree |
| 2006/0064169 A1 | 3/2006 | Ferree |
| 2006/0069439 A1 | 3/2006 | Zucherman et al. |
| 2006/0116768 A1 | 6/2006 | Krueger et al. |
| 2006/0142858 A1 | 6/2006 | Colleran et al. |
| 2006/0142862 A1 | 6/2006 | Diaz et al. |
| 2006/0155378 A1 | 7/2006 | Eckman |
| 2006/0167549 A1 | 7/2006 | Mathys, Jr. et al. |
| 2006/0178744 A1 | 8/2006 | De et al. |
| 2006/0178746 A1 | 8/2006 | Bartish, Jr. et al. |
| 2006/0195097 A1 | 8/2006 | Evans et al. |
| 2006/0200239 A1 | 9/2006 | Rothman et al. |
| 2006/0224241 A1 | 10/2006 | Butler et al. |
| 2006/0235426 A1 | 10/2006 | Lim et al. |
| 2006/0235525 A1 | 10/2006 | Gil et al. |
| 2006/0235527 A1 | 10/2006 | Buettner-Janz et al. |
| 2006/0241641 A1 | 10/2006 | Albans et al. |
| 2006/0241766 A1 | 10/2006 | Felton et al. |
| 2006/0259144 A1 | 11/2006 | Trieu |
| 2006/0259146 A1 | 11/2006 | Navarro et al. |
| 2006/0265068 A1 | 11/2006 | Schwab |
| 2006/0265077 A1 | 11/2006 | Zwirkoski |
| 2006/0287728 A1 | 12/2006 | Mokhtar et al. |
| 2006/0293752 A1 | 12/2006 | Moumene et al. |
| 2006/0293753 A1 | 12/2006 | Thramann |
| 2006/0293754 A1 | 12/2006 | Devilliers et al. |
| 2007/0010826 A1 | 1/2007 | Rhoda et al. |
| 2007/0021837 A1 | 1/2007 | Ashman |
| 2007/0032875 A1 | 2/2007 | Blacklock et al. |
| 2007/0067035 A1 | 3/2007 | Falahee |
| 2007/0067036 A1 | 3/2007 | Hudgins et al. |
| 2007/0073398 A1 | 3/2007 | Fabian et al. |
| 2007/0093898 A1 | 4/2007 | Schwab et al. |
| 2007/0100453 A1 | 5/2007 | Parsons et al. |
| 2007/0100454 A1* | 5/2007 | Burgess ............... A61B 17/025 623/17.14 |
| 2007/0100456 A1 | 5/2007 | Dooris et al. |
| 2007/0123903 A1 | 5/2007 | Raymond et al. |
| 2007/0123904 A1 | 5/2007 | Stad et al. |
| 2007/0135923 A1 | 6/2007 | Peterman et al. |
| 2007/0162133 A1 | 7/2007 | Doubler et al. |
| 2007/0168033 A1 | 7/2007 | Kim et al. |
| 2007/0168036 A1 | 7/2007 | Ainsworth et al. |
| 2007/0179615 A1 | 8/2007 | Heinz et al. |
| 2007/0185578 A1 | 8/2007 | O'Neil et al. |
| 2007/0213821 A1 | 9/2007 | Kwak et al. |
| 2007/0233077 A1 | 10/2007 | Khalili |
| 2007/0233247 A1 | 10/2007 | Schwab |
| 2007/0233248 A1 | 10/2007 | Schwab et al. |
| 2007/0233251 A1 | 10/2007 | Abdou |
| 2007/0270970 A1 | 11/2007 | Trieu |
| 2007/0282449 A1 | 12/2007 | De et al. |
| 2007/0299521 A1 | 12/2007 | Glenn et al. |
| 2008/0015698 A1 | 1/2008 | Marino et al. |
| 2008/0015701 A1 | 1/2008 | Garcia et al. |
| 2008/0021557 A1 | 1/2008 | Trieu |
| 2008/0051900 A1 | 2/2008 | De et al. |
| 2008/0051901 A1 | 2/2008 | De et al. |
| 2008/0125864 A1 | 5/2008 | De et al. |
| 2008/0125865 A1 | 5/2008 | Abdelgany et al. |
| 2008/0133011 A1 | 6/2008 | De et al. |
| 2008/0154301 A1 | 6/2008 | De et al. |
| 2008/0154382 A1 | 6/2008 | De et al. |
| 2008/0215155 A1 | 9/2008 | De et al. |
| 2008/0221696 A1 | 9/2008 | De et al. |
| 2008/0228274 A1 | 9/2008 | De et al. |
| 2008/0228277 A1 | 9/2008 | De et al. |
| 2008/0294259 A1 | 11/2008 | De et al. |
| 2009/0043391 A1 | 2/2009 | De et al. |
| 2009/0048674 A1 | 2/2009 | Zubok et al. |
| 2009/0048677 A1 | 2/2009 | McLeod et al. |
| 2009/0076614 A1 | 3/2009 | Arramon |
| 2009/0105833 A1 | 4/2009 | Hovda et al. |
| 2009/0105834 A1 | 4/2009 | Hovda et al. |
| 2009/0105835 A1 | 4/2009 | Hovda et al. |
| 2009/0192617 A1 | 7/2009 | Arramon et al. |
| 2009/0205188 A1 | 8/2009 | De et al. |
| 2009/0210060 A1 | 8/2009 | De et al. |
| 2009/0222101 A1 | 9/2009 | De et al. |
| 2009/0276051 A1 | 11/2009 | Arramon et al. |
| 2009/0326656 A1 | 12/2009 | De et al. |
| 2010/0004746 A1 | 1/2010 | Arramon |
| 2010/0016972 A1 | 1/2010 | Jansen et al. |
| 2010/0016973 A1 | 1/2010 | De et al. |
| 2010/0030335 A1 | 2/2010 | Arramon |
| 2010/0049040 A1 | 2/2010 | De et al. |
| 2010/0069976 A1 | 3/2010 | De et al. |
| 2010/0076558 A1 | 3/2010 | De et al. |
| 2010/0087868 A1 | 4/2010 | Barr et al. |
| 2010/0179419 A1 | 7/2010 | De et al. |
| 2011/0004313 A1 | 1/2011 | De et al. |
| 2011/0270261 A1* | 11/2011 | Mast ..................... A61F 2/4611 606/99 |
| 2013/0297026 A1 | 11/2013 | De et al. |
| 2015/0148908 A1* | 5/2015 | Marino ................. A61F 2/4455 623/17.16 |
| 2017/0079809 A1 | 3/2017 | De et al. |

(56) References Cited

U.S. PATENT DOCUMENTS

FOREIGN PATENT DOCUMENTS

| | | |
|---|---|---|
| EP | 0333990 A2 | 9/1989 |
| EP | 0333990 A3 | 5/1990 |
| EP | 0560140 A1 | 9/1993 |
| EP | 0560141 A1 | 9/1993 |
| EP | 0591712 A1 | 4/1994 |
| EP | 0820740 A1 | 1/1998 |
| EP | 1142544 A1 | 10/2001 |
| EP | 1153582 A2 | 11/2001 |
| EP | 1153582 A3 | 11/2001 |
| EP | 1250898 A1 | 10/2002 |
| EP | 1306064 A1 | 5/2003 |
| EP | 1344493 A1 | 9/2003 |
| EP | 1344506 A1 | 9/2003 |
| EP | 1344507 A1 | 9/2003 |
| EP | 1344508 A1 | 9/2003 |
| EP | 1417940 A1 | 5/2004 |
| EP | 1570813 A1 | 9/2005 |
| FR | 2803741 A1 | 7/2001 |
| JP | S61122859 A | 6/1986 |
| JP | S63164948 A | 7/1988 |
| WO | WO-9920209 A1 | 4/1999 |
| WO | WO-9930651 A1 | 6/1999 |
| WO | WO-0004851 A1 | 2/2000 |
| WO | WO-0035384 A1 | 6/2000 |
| WO | WO-0042954 A2 | 7/2000 |
| WO | WO-0042954 A3 | 11/2000 |
| WO | WO-0101893 A1 | 1/2001 |
| WO | WO-0115637 A1 | 3/2001 |
| WO | WO-0168003 A1 | 9/2001 |
| WO | WO-0211650 A2 | 2/2002 |
| WO | WO-0211650 A3 | 9/2003 |
| WO | WO-2004000170 A1 | 12/2003 |
| WO | WO-2004000171 A1 | 12/2003 |
| WO | WO-2004026187 A1 | 4/2004 |
| WO | WO-2004041131 A2 | 5/2004 |
| WO | WO-2004054477 A1 | 7/2004 |
| WO | WO-2004066884 A1 | 8/2004 |
| WO | WO-2004041131 A3 | 9/2004 |
| WO | WO-2005004756 A2 | 1/2005 |
| WO | WO-2005004756 A3 | 5/2005 |
| WO | WO-2005053580 A1 | 6/2005 |
| WO | WO-2005072662 A1 | 8/2005 |
| WO | WO-2005112833 A1 | 12/2005 |
| WO | WO-2005112834 A2 | 12/2005 |
| WO | WO-2005112834 A3 | 5/2006 |
| WO | WO-2006119092 A2 | 11/2006 |
| WO | WO-2006119092 A3 | 12/2006 |
| WO | WO-2007121320 A2 | 10/2007 |
| WO | WO-2007121320 A3 | 6/2008 |
| ZA | 20039312 | 11/2003 |

OTHER PUBLICATIONS

Hellier, et al., Wear Studies for Development of an Intervertebral Disc Prosthesis. Spine, vol. 17 No. 6 Supplement pp. 86-96 (1992).
International search report and written opinion dated Dec. 23, 2008 for PCT/US2008/071551.
Lee, et al. Impact Response of the Intervertebral Disc in a Finite-Element Model. Spine. 2000; 25(19):2431-2439.
Lehuec, et al. Shock Absorption in Lumber Disc Prosthesis. Journal of Spinal Disorders & Techniques. 2003; 16(4):346-351.
Notice of allowance dated Apr. 16, 2013 for U.S. Appl. No. 12/883,068.
Notice of allowance dated May 15, 2017 for U.S. Appl. No. 15/368,437.
Notice of allowance dated Oct. 12, 2016 for U.S. Appl. No. 13/941,121.
Office action dated Feb. 4, 2016 for U.S. Appl. No. 13/941,121.
Office action dated Mar. 12, 2012 for U.S. Appl. No. 12/883,068.
Office action dated Apr. 28, 2011 for U.S. Appl. No. 11/836,684.
Office action dated Sep. 15, 2010 for U.S. Appl. No. 11/836,684.
Office action dated Oct. 15, 2012 for U.S. Appl. No. 12/883,068.
Office action dated Jul. 15, 2016 for U.S. Appl. No. 13/941,121.

* cited by examiner

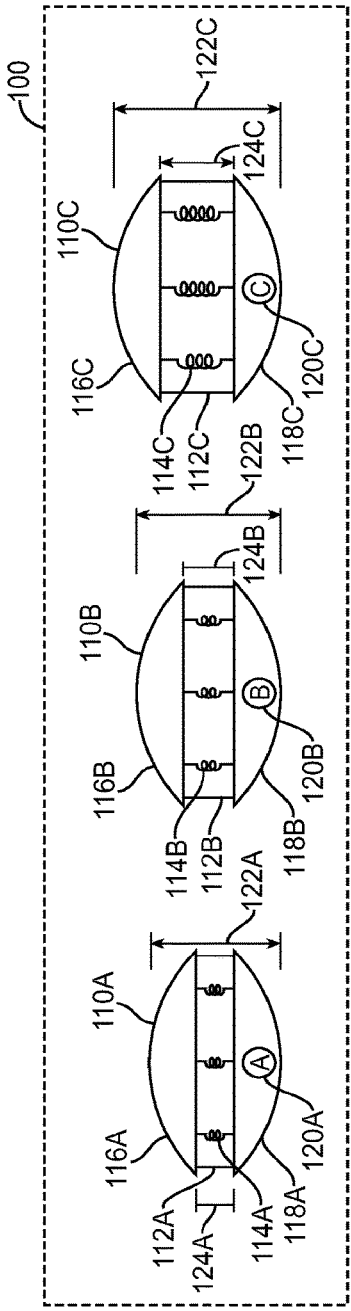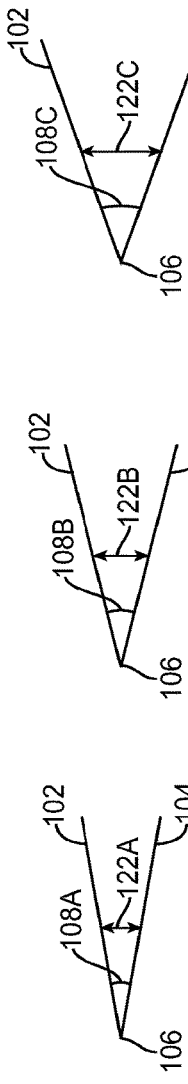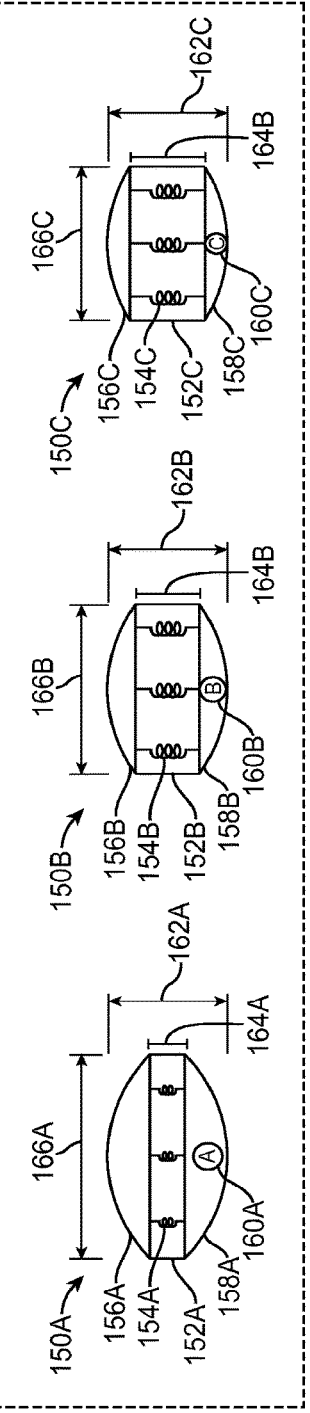

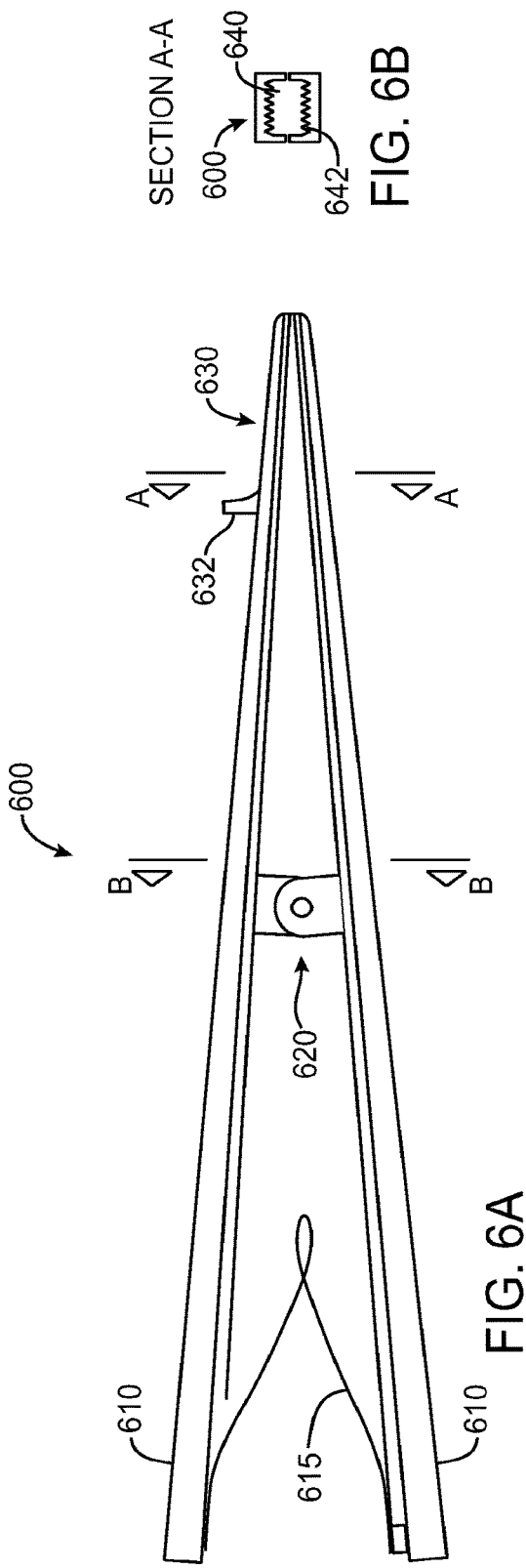
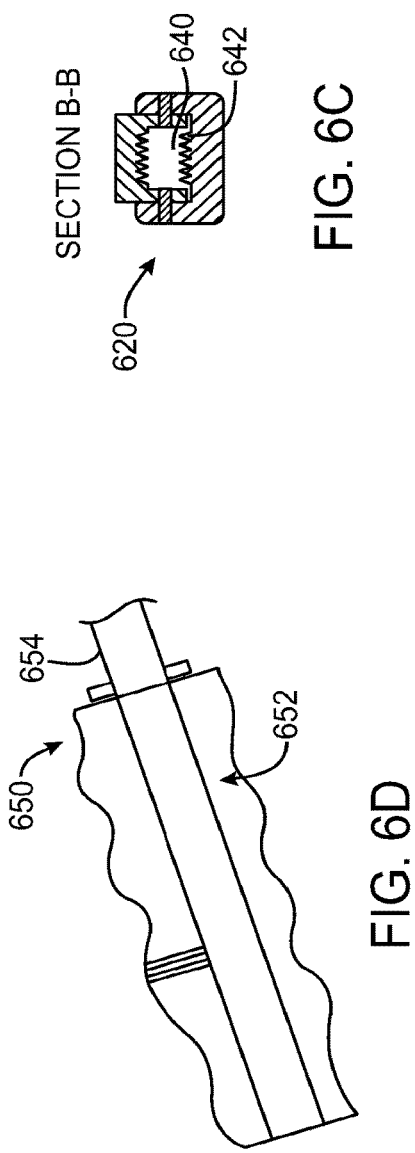
FIG. 6A
FIG. 6B
FIG. 6C
FIG. 6D

CUSTOMIZED INTERVERTEBRAL PROSTHETIC DISC WITH SHOCK ABSORPTION

CROSS-REFERENCES TO RELATED APPLICATIONS

The present application is a continuation of U.S. patent application Ser. No. 15/368,437, filed Dec. 2, 2016, now U.S. Pat. No. 9,687,355, which is a continuation of U.S. patent application Ser. No. 13/941,121, filed Jul. 12, 2013, which is a divisional of U.S. patent application Ser. No. 12/883,068, filed Sep. 15, 2010, now U.S. Pat. No. 8,506,631, which is a divisional of U.S. patent application Ser. No. 11/836,684, filed Aug. 9, 2007; the full disclosures of each are incorporated herein by reference in its entirety.

BACKGROUND OF THE INVENTION

The present invention relates to medical devices and methods. More specifically, the invention relates to intervertebral disc prostheses.

Back pain takes an enormous toll on the health and productivity of people around the world. According to the American Academy of Orthopedic Surgeons, approximately 80 percent of Americans will experience back pain at some time in their life. In just the year 2000, approximately 26 million visits were made to physicians' offices due to back problems in the United States. On any one day, it is estimated that 5% of the working population in America is disabled by back pain.

One common cause of back pain is injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs.

Discs often become damaged due to wear and tear or acute injury. For example, discs may bulge (herniate), tear, rupture, degenerate or the like. A bulging disc may press against the spinal cord or a nerve exiting the spinal cord, causing "radicular" pain (pain in one or more extremities caused by impingement of a nerve root). Degeneration or other damage to a disc may cause a loss of "disc height," meaning that the natural space between two vertebrae decreases. Decreased disc height may cause a disc to bulge, facet loads to increase, two vertebrae to rub together in an unnatural way and/or increased pressure on certain parts of the vertebrae and/or nerve roots, thus causing pain. In general, chronic and acute damage to intervertebral discs is a common source of back related pain and loss of mobility.

When one or more damaged intervertebral discs cause a patient pain and discomfort, surgery is often required. Traditionally, surgical procedures for treating intervertebral discs have involved discectomy (partial or total removal of a disc), with or without fusion of the two vertebrae adjacent to the disc. Fusion of the two vertebrae is achieved by inserting bone graft material between the two vertebrae such that the two vertebrae and the graft material grow together. Oftentimes, pins, rods, screws, cages and/or the like are inserted between the vertebrae to act as support structures to hold the vertebrae and graft material in place while they permanently fuse together. Although fusion often treats the back pain, it reduces the patient's ability to move, because the back cannot bend or twist at the fused area. In addition, fusion increases stresses at adjacent levels of the spine, potentially accelerating degeneration of these discs.

In an attempt to treat disc related pain without fusion, an alternative approach has been developed, in which a movable, implantable, artificial intervertebral disc (or "disc prosthesis") is inserted between two vertebrae. A number of different intervertebral disc prostheses are currently being developed. For example, the inventors of the present invention have developed disc prostheses described in U.S. patent application Ser. Nos. 10/855,817 and 10/855,253, previously incorporated by reference. Other examples of intervertebral disc prostheses are the LINK® SB Charite disc (provided by DePuy Spine, Inc.) Mobidisk® (provided by LDR Medical (www.ldrmedical.fr)), the Bryan Cervical Disc (provided by Medtronic Sofamor Danek, Inc.), the ProDisc® or ProDisc-C® (from Synthes Stratec, Inc.), and the PCM disc (provided by Cervitech, Inc.). Although existing disc prostheses provide advantages over traditional treatment methods, improvements are ongoing.

Work in relation to the present invention suggests that current prosthesis and methodologies may be less than ideal. For example, some disc prostheses may only partially restore patient motion in some patients. Also, some disc prostheses may potentially provide more motion postoperatively than might occur naturally for an individual patient, depending on his or her individual characteristics. For example, older patients may have a smaller range of motion between vertebrae than younger patients, and a prosthesis with an appropriate range of motion for a younger patient may provide an excessive range of motion for an older patient. Younger active patients may place a greater load on a disc prosthesis, and current prostheses may be less than ideal for restoring motion between the vertebrae in a manner that fully accommodates such active patients.

Therefore, a need exists for improved intervertebral disc prostheses. Ideally, such improved prostheses would avoid at least some of the short comings of the present prostheses.

BRIEF SUMMARY OF THE INVENTION

Embodiments of the present invention provide customizable intervertebral prostheses systems and methods. The prosthesis system comprises supports that can be positioned against vertebrae and a selected resilient core that can be positioned between the supports to allow the supports to articulate. The resilient core can be selected from a plurality of cores in response to patient characteristics, such as age and/or intervertebral mobility, such that the prosthesis implanted in the patient is tailored to the needs of the patient. The plurality of cores comprise cores with different resiliencies, and one of the cores can be selected such that the upper and lower supports articulate with the desired shock absorbing resiliency and/or maximum angle of inclination when the selected core is positioned between the supports. The shock absorbing core may be compressed during insertion into the intervertebral space to minimize distraction between the vertebrae. The supports can comprise known support plates and may comprise, in some embodiments, in situ expandable supports to minimize the invasiveness of the procedure.

In a first aspect an intervertebral disc prosthesis system is provided. The system comprises a plurality of selectable cores. Each core comprises upper and lower surfaces and at least one of a resilient material or a resilient member disposed between the upper and lower surfaces to allow the upper and lower surfaces to move resiliently toward and away from each other. The system also comprises upper and lower supports that are locatable about the core. Each support comprises an outer surface which engages a vertebra and an inner surface that is shaped to contact one of the surfaces of each core. Each core of the plurality comprises a different resiliency. The upper and lower supports are adapted to articulate when one of the cores is selected and positioned between the upper and lower supports.

In many embodiments, each core is identifiable with an indicia, such that each core is selectable in response to the indicia and a patient characteristic. The indicia may comprise at least one of a color of the core, a marking on the core, a height of the core, or a width of the core. In specific embodiments, the indicia of each core corresponds to a resiliency of the core and a maximum angle of inclination between the supports when the core is positioned between the supports.

In many embodiments, each core of the plurality comprises a different dimension to limit a maximum angle of inclination between the upper and lower supports in response to the patient characteristic. The different dimension may comprise at least one of a height or a width.

In many embodiments, the upper surface of each core comprises a curved surface to slide against the inner surface of the upper support. In specific embodiments, lower surface of each core may be capable of attachment to the lower support. In some embodiments, the lower surface of each core comprises a curved surface to slide against the inner surface of the lower support.

In many embodiments, each core comprises an upper component with the upper surface disposed thereon and a lower component with the lower surface disposed thereon. The upper and lower core components of each core can be configured to slide relative to one another in response to loading when positioned between the upper and lower supports, for example loading caused by patient activity. In specific embodiments, the upper and lower components of each core are configured to slide relative to one another with telescopic motion.

In some embodiments, the upper support comprises a upper plate and the lower support comprises a lower plate.

In some embodiments, the upper support comprises an upper expandable support and the lower support comprises a lower expandable support.

In some embodiments, several cores of the plurality comprises the same height and different resiliencies, such that a maximum angle of inclination between the plates is substantially the same for the several cores.

In many embodiments, the plurality of selectable cores comprises cores with a maximum compression within a range from about ⅓ mm to about 1 mm.

In another aspect, an intervertebral disc prosthesis system is provided. The intervertebral disc prosthesis system comprises a plurality of selectable cores. Each core comprises upper and lower curved surfaces. At least one of a resilient material or a resilient member is disposed between the upper and lower curved surfaces to allow the upper and lower surfaces to move resiliently toward and away from each other. The system also comprises upper and lower supports that are locatable about the core. Each support comprises an outer surface, which engages a vertebra, and an inner curved surface shaped to slide over one of the curved surfaces of each core. Each core of the plurality comprises a different resiliency. The upper and lower supports are adapted to articulate when one of the cores is selected and positioned between the upper and lower supports.

In many embodiments, each core is identifiable with an indicia, such that each core is selectable in response to the indicia and a patient characteristic. The indicia may comprise at least one of a color of the core, a marking on the core, a height of the core, or a width of the core. In specific embodiments, the indicia of each core corresponds to a resiliency of the core and a maximum angle of inclination between the supports when the core is positioned between the supports.

In many embodiments, the at least one resilient material comprises a polymer. The at least one resilient material may comprise a hydrogel. The at least one resilient support member may be disposed within the resilient material and attached to the upper and lower curved surfaces.

In many embodiments, the at least one resilient support member comprises a plurality of springs.

In many embodiments, the upper and lower curved surfaces of the core comprise at least one of a polymer, a ceramic and a metal. The metal may comprise at least one of cobalt chrome molybdenum, titanium or stainless steel.

In another aspect, a method of assembling an intervertebral prosthesis for insertion into a patient is provided. A resilient core is selected from among a plurality of resilient cores. The core is placed between first and second supports. The core is selected in response to a resiliency of the core and a patient characteristic.

In many embodiments, the selected core is identified with an indicia and selected in response to the indicia and a patient characteristic. The indicia may comprise at least one of a color of the core, a marking on the core, a height of the core, or a width of the core. In specific embodiments, the indicia of each core corresponds to a resiliency of the core and a maximum angle of inclination between the supports when the core is positioned between the supports.

In many embodiments, the first and second supports articulate when the core is positioned between the supports. The core may comprise first and second components that slide relative to each other when the core is loaded.

In many embodiments, the core is selected in response to a maximum angle of inclination when the core is positioned between the supports.

In another aspect, a method of inserting an intervertebral prosthesis into an intervertebral space between vertebrae of a patient is provided. A shock absorbing core is compressed from an expanded profile configuration to a narrow profile configuration when the core is inserted into the intervertebral space. The shock absorbing core can articulate an upper support and a lower support when positioned between the upper support and the lower support.

In many embodiments, the upper support and the lower support are positioned in the intervertebral space, and the shock absorbing core is inserted between the upper support and the lower support while the upper support and the lower support are positioned in the intervertebral space. In specific embodiments, shock absorbing core locks into place within the upper plate or the lower plate.

In many embodiments, the core is positioned between the upper support and the lower support when the upper support and the lower support are inserted into the intervertebral space. In specific embodiments, the upper support and the lower support articulate when the upper support and the lower support are inserted into the intervertebral space.

In some embodiments, the shock absorbing core is compressed with an instrument when the core is inserted into the intervertebral space. The shock absorbing core can be compressed by at least about 0.5 mm when the core is inserted into the intervertebral space.

In another aspect, an intervertebral disc prosthesis is provided. The prosthesis comprises a resilient core. The core comprises an upper component with an upper surface and a lower component with a lower surface. At least one of a resilient material or a resilient member is disposed between the upper and lower components so as to allow the upper and lower components to move resiliently toward and away from each other. The upper and lower components define an inner chamber of the core. At least one channel extends from the inner chamber to an external surface of the core to allow the passage of fluid through the chamber. The prosthesis also comprises upper and lower supports locatable about the core. Each support comprises an outer surface which engages a vertebra, and an inner surface shaped to contact one of the surfaces of the core. The upper and lower supports are adapted to articulate when the core is positioned between the upper and lower supports.

In some embodiments, the at least one channel comprises at least two channels that extend from the chamber to the external surface of the core to pass fluid through the core. the at least one channel can be adapted to pump fluid out of the core when the components move toward each other and draw fluid into the core when the components move away from each other.

In another aspect, an instrument for insertion of a intervertebral disc prosthesis into an intervertebral space is provided. The instrument comprises a distractor tip that comprises a channel dimensioned to pass the prosthesis. The instrument also comprises at least one of a resilient member or a resilient material to compress the prosthesis from an expanded profile configuration to a narrow profile configuration with the distractor tip when the prosthesis slides along the channel toward the intervertebral space.

In many embodiments, a pair of handles is connected to the distractor tip. The resilient member comprises a spring connected to the handles to drive the handles apart and compress the prosthesis to the narrow profile configuration.

In another aspect, a system for insertion of an intervertebral disc prosthesis into an intervertebral space is provided. The system comprises a plurality of selectable shock absorbing intervertebral disc prosthesis cores, and an instrument. The instrument comprises a distractor tip with a channel dimensioned to pass the prosthesis. The distractor tip is capable of compressing at least one of the plurality of cores from an expanded profile configuration to a narrow profile configuration when the prosthesis slides along the channel toward the intervertebral space.

In many embodiments, the expanded profile configuration comprises an unloaded configuration of the at least one of the plurality of cores, and the narrow profile configuration comprises a maximum loaded compression of the at least one of the plurality of cores.

BRIEF DESCRIPTION OF THE DRAWINGS

FIG. 1D shows a plurality of selectable shock absorbing cores with differing heights and differing resiliencies, according to embodiments of the present invention;

FIG. 1E schematically illustrates a first maximum angle of inclination with the first shock absorbing core of FIG. 1D positioned between endplates;

FIG. 1F schematically illustrates a second maximum angle of inclination with the second shock absorbing core of FIG. 1D positioned between the endplates;

FIG. 1G schematically illustrates a third maximum angle of inclination with the third shock absorbing core of FIG. 1D positioned between the endplates;

FIG. 1H shows a plurality of selectable shock absorbing cores with differing widths and differing resiliencies, according to embodiments of the present invention;

FIGS. 6A to 6D show a placement instrument 600 capable of compressing the core when the implant is inserted into the intervertebral space, according to embodiments of the present invention.

DETAILED DESCRIPTION OF THE INVENTION

Various embodiments of the present invention generally provide for an intervertebral disc prosthesis having upper and lower plates disposed about a selectable core. The selectable core includes a resilient material, which allows the core to absorb forces applied to it by vertebrae. The shock absorbing cores can be used with many prosthesis and approaches to the intervertebral disc space including anterior, lateral, posterior and posterior lateral approaches. Although various embodiments of such a prosthesis are shown in the figures and described further below, the general principles of these embodiments, namely selecting a core with a force absorbing material in response to patient needs, may be applied to any of a number of other disc prostheses, such as but not limited to the LINK® SB Charite disc (provided by DePuy Spine, Inc.) Mobidisk® (provided by LDR Medical (www.ldrmedical.fr)), the Bryan Cervical Disc and Maverick Lumbar Disc (provided by Medtronic Sofamor Danek, Inc.), the ProDisc® or ProDisc-C® (from Synthes Stratec, Inc.), and the PCM disc (provided by Cervitech, Inc.). In some embodiments, the selectable core can be used with an expandable intervertebral prosthesis, as described in U.S. application Ser. No. 11/787,110, entitled "Posterior Spinal Device and Method", filed Apr. 12, 2007, the full disclosure of which is incorporated herein by reference.

Figure 1A:
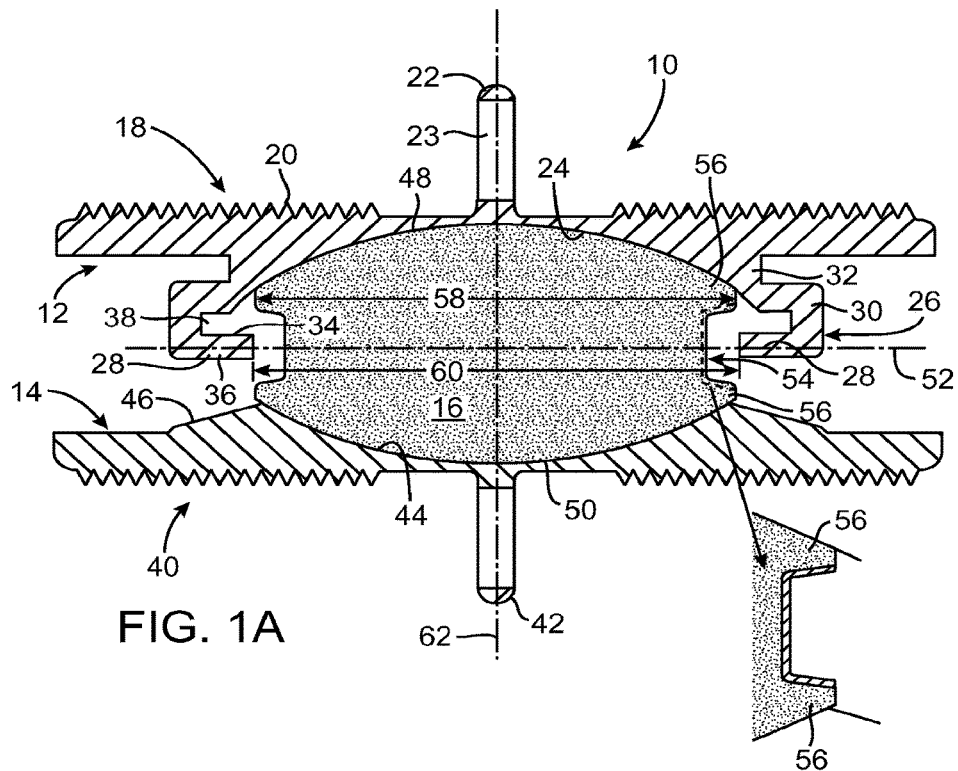
FIG. 1A is a cross-sectional anterior view of an intervertebral disc prosthesis with the prosthesis plates and selected core in vertical alignment, according to embodiments of the present invention.
Figure 1B:
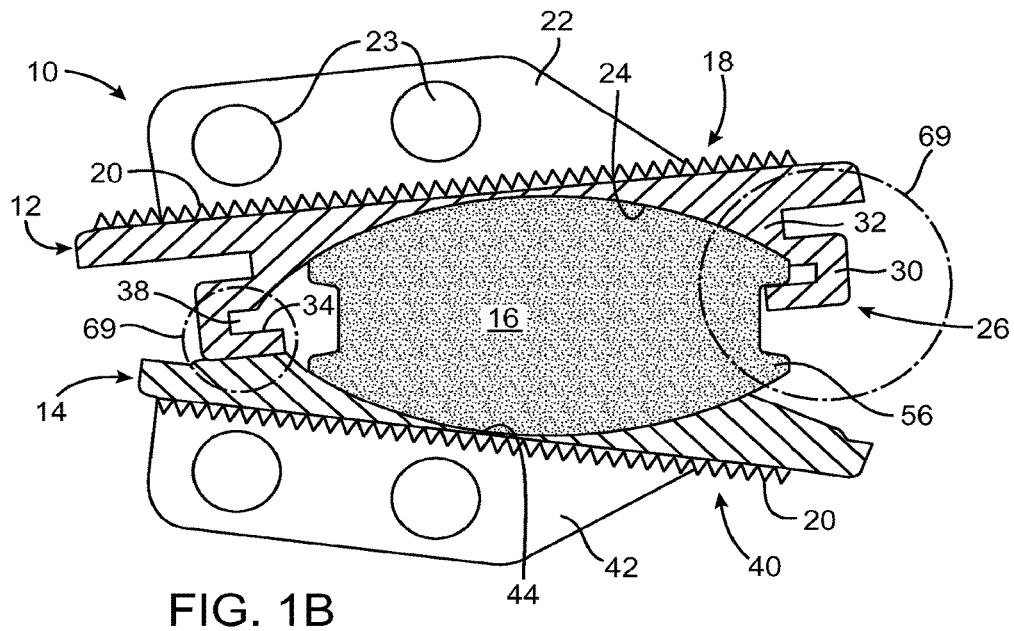
FIG. 1B is a side view of the prosthetic disc in FIG. 1 after sliding movement of the plates over the selected core.
Figure 1C:
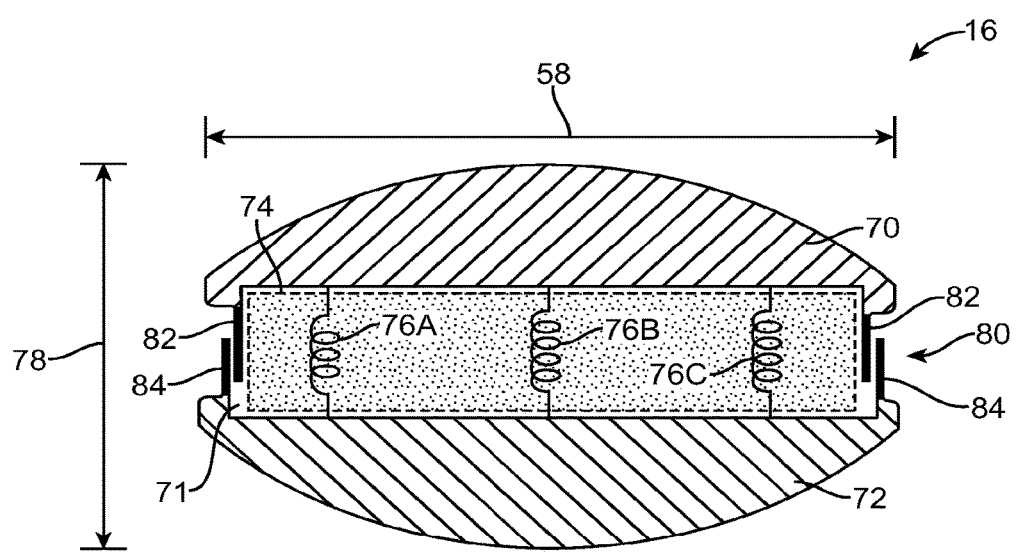
FIG. 1C is a cross-sectional view a the selected shock absorbing cores shown in detail, according to embodiments of the present invention.

FIGS. 1A to 1C show a prosthetic disc 10 comprising a selected shock absorbing core, according to embodiments of the present invention. Disc 10 for intervertebral insertion between two adjacent spinal vertebrae (not shown) suitably includes an upper plate 12, a lower plate 14 and a selected shock absorbing core 16 located between the plates. The upper plate 12 includes an outer surface 18 and an inner surface 24 and may be constructed from any suitable metal, alloy or combination of metals or alloys, such as but not limited to cobalt chrome molybdenum, titanium (such as grade 5 titanium), stainless steel and/or the like. In one embodiment, typically used in the lumbar spine, the upper plate 12 is constructed of cobalt chrome molybdenum, and the outer surface 18 is treated with aluminum oxide blasting followed by a titanium plasma spray. In another embodiment, typically used in the cervical spine, the upper plate 12 is constructed of titanium, the inner surface 24 is coated with titanium nitride, and the outer surface 18 is treated with aluminum oxide blasting. An alternative cervical spine embodiment includes no coating on the inner surface 24. In other cervical and lumbar disc embodiments, any other suitable metals or combinations of metals may be used. In some embodiments, it may be useful to couple two materials together to form the inner surface 24 and the outer surface 18. For example, the upper plate 12 may be made of an MRI-compatible material, such as titanium, but may include a harder material, such as cobalt chrome molybdenum, for the inner surface 24. In another embodiment, upper plated 12 may comprise a metal, and inner surface 24 may comprise a ceramic material. All combinations of materials are contemplated within the scope of the present invention. Any suitable technique may be used to couple materials together, such as snap fitting, slip fitting, lamination, interference fitting, use of adhesives, welding and/or the like. Any other suitable combination of materials and coatings may be employed in various embodiments of the invention.

In some embodiments, the outer surface 18 is planar. Oftentimes, the outer surface 18 will include one or more surface features and/or materials to enhance attachment of the prosthesis 10 to vertebral bone. For example, the outer surface 18 may be machined to have serrations 20 or other surface features for promoting adhesion of the upper plate 12 to a vertebra. In the embodiment shown, the serrations 20 extend in mutually orthogonal directions, but other geometries would also be useful. Additionally, the outer surface 18 may be provided with a rough microfinish formed by blasting with aluminum oxide microparticles or the like. In some embodiments, the outer surface may also be titanium plasma sprayed to further enhance attachment of the outer surface 18 to vertebral bone.

The outer surface 18 may also carry an upstanding, vertical fin 22 extending in an anterior-posterior direction. The fin 22 is pierced by transverse holes 23. In alternative embodiments, the fin 22 may be rotated away from the anterior-posterior axis, such as in a lateral-lateral orientation, a posterolateral-anterolateral orientation, or the like. In some embodiments, the fin 22 may extend from the surface 18 at an angle other than 90.degree. Furthermore, multiple fins 22 may be attached to the surface 18 and/or the fin 22 may have any other suitable configuration, in various embodiments. In some embodiments, such as discs 10 for cervical insertion, the fins 22, 42 may be omitted altogether.

The inner, spherically curved concave surface 24 is formed at a central (from right to left), axial position with a circular recess 26 as illustrated. At the outer edge of the curved surface 24, the upper plate 12 carries peripheral restraining structure comprising an integral ring structure 26 including an inwardly directed rib or flange 28. The flange 28 forms part of a U-shaped member 30 joined to the major part of the plate by an annular web 32. The flange 28 has an inwardly tapering shape and defines upper and lower surfaces 34 and 36 respectively which are inclined slightly relative to the horizontal when the upper plate 12 is at the orientation seen in FIG. 1. An overhang 38 of the U-shaped member 30 has a vertical dimension that tapers inwardly as illustrated.

The lower plate 14 is similar to the upper plate 12 except for the absence of the peripheral restraining structure 26. Thus, the lower plate 14 has an outer surface 40 which is planar, serrated and microfinished like the outer surface 18 of the upper plate 12. The lower plate 14 optionally carries a fin 42 similar to the fin 22 of the upper plate. The inner surface 44 of the lower plate 14 is concavely, spherically curved with a radius of curvature matching that of the inner surface 24 of the upper plate 12. Once again, this surface may be provided with a titanium nitride or other finish.

At the outer edge of the inner curved surface 44, the lower plate 14 is provided with an inclined ledge formation 46. Alternatively, the lower plate 14 may include peripheral restraining structure analogous to the peripheral restraining structure 26 on the upper plate 12.

The selected shock absorbing core 16 is symmetrical about a central, equatorial plane 52 which bisects it laterally. (Although in other embodiments, the selected shock absorbing core 16 may be asymmetrical.) Lying on this equatorial plane is an annular recess or groove 54 which extends about the periphery of the selected shock absorbing core. The groove 54 is defined between upper and lower ribs or lips 56. When the plates 12, 14 and selected shock absorbing core 16 are assembled and in the orientation seen in FIG. 1, the flange 28 lies on the equatorial plane and directly aligned with the groove 54. The outer diameter 58 of the lips 56 is preferably very slightly larger than the diameter 60 defined by the inner edge of the flange 28. In some embodiments, the selected shock absorbing core 16 is movably fitted into the upper plate 12 via an interference fit. To form such an interference fit with a metal component of selected core 16 and metal plate 12, any suitable techniques may be used. For example, the plate 12 may be heated so that it expands, and the component of selected core 16 may be dropped into the plate 12 in the expanded state. When the plate 12 cools and contracts, the interference fit is created. In another embodiment, the upper plate 12 may be formed around the component of selected shock absorbing core 16. Alternatively, the selected shock absorbing core 16 and upper plate 12 may include complementary threads, which allow the selected shock absorbing core 16 to be screwed into the upper plate 12, where it can then freely move.

The central axis of the disc 10 (the axis passing through the centers of curvature of the curved surfaces) is indicated with the reference numeral 62. As shown in FIG. 1, the disc 10 may be symmetrical about a central anterior-posterior plane containing the axis 62. In some embodiments the axis 62 is posteriorly disposed, i.e. is located closer to the posterior limit of the disc than the anterior limit thereof.

In use, the disc 10 is surgically implanted between adjacent spinal vertebrae in place of a damaged disc. The adjacent vertebrae are forcibly separated from one another to provide the necessary space for insertion. The disc 10 is typically, though not necessarily, advanced toward the disc space from an anterolateral or anterior approach and is inserted in a posterior direction—i.e., from anterior to posterior. The disc is inserted into place between the vertebrae with the fins 22, 42 of the plates 12, 14 entering slots cut in the opposing vertebral surfaces to receive them. During and/or after insertion, the vertebrae, facets, adjacent ligaments and soft tissues are allowed to move together to hold the disc in place. The serrated and microfinished surfaces 18, 40 of the plates 12, 14 locate against the opposing vertebrae.

The serrations 20 and fins 22, 42 provide initial stability and fixation for the disc 10. With passage of time, enhanced by the titanium surface coating, firm connection between the plates and the vertebrae will be achieved as bone tissue grows over the serrated surface. Bone tissue growth will also take place about the fins 22, 40 and through the transverse holes 23 therein, further enhancing the connection which is achieved.

In the assembled disc 10, the complementary and cooperating spherical surfaces of the plates and selected shock absorbing core allow the plates to slide or articulate over the selected core through a fairly large range of angles and in all directions or degrees of freedom, including rotation about the central axis 62. FIG. 1A shows the disc 10 with the plates 12 and 14 and selected shock absorbing core 16 aligned vertically with one another on the axis 62. FIG. 1B illustrates a situation where maximum anterior flexion of the disc 10 has taken place. At this position, the upper rib 56 has entered the hollow 38 of the U-shaped member 30, the lower surface of the rib 56 has moved into contact with the upper surface 34 of the flange 28, the flange having moved into the groove 54, and the lower surface 36 of the flange has moved into contact with the upper surface of the ledge formation 46, as will be seen in the encircled areas 69. Abutment between the various surfaces prevents further anterior flexure. The design also allows for the inner extremity of the flange 28 to abut against the base of the groove 54, thereby limiting further relative movement between the selected core and plate. A similar configuration is achieved in the event of maximum posterior flexure of the plates 12, 14 over the selected shock absorbing core, such as during spinal extension and/or in the event of maximum lateral flexure.

The flange 28 and the groove 54 defined between the ribs 56, prevent separation of the selected core from the plates. In other words, the cooperation of the retaining formations ensures that the selected shock absorbing core is held captive between the plates at all times during flexure of the disc 10.

In an alternative embodiment, the continuous annular flange 28 may be replaced by a retaining formation comprising a number of flange segments which are spaced apart circumferentially. Such an embodiment could include a single, continuous groove 54 as in the illustrated embodiment. Alternatively, a corresponding number of groove-like recesses spaced apart around the periphery of the selected core could be used, with each flange segment opposing one of the recesses. In another embodiment, the continuous flange or the plurality of flange segments could be replaced by inwardly directed pegs or pins carried by the upper plate 12. This embodiment could include a single, continuous groove 54 or a series of circumferentially spaced recesses with each pin or peg opposing a recess.

In yet another embodiment, the retaining formation(s) can be carried by the lower plate 14 instead of the upper plate, i.e. the plates are reversed. In some embodiments, the upper (or lower) plate is formed with an inwardly facing groove, or circumferentially spaced groove segments, at the edge of its inner, curved surface, and the outer periphery of the selected core is formed with an outwardly facing flange or with circumferentially spaced flange segments.

Referring now to FIG. 1C, a cross-sectional view of a selected shock absorbing core 16 is shown in detail. Core 16 comprises an upper component 70 and a lower component 72. Upper component 70 and lower component 72 define a chamber 71. A resilient material 74 can be positioned between upper component 70 and lower component 72 within chamber 71. Resilient material 74 may extend between from one component to the other to component, such that upper component 70 is supported with the resilient material. Resilient material 74 may comprise many known resilient materials, for example an elastomer such as siloxane. At least one resilient member can be positioned between upper component 70 and lower component 72. The at least one resilient member may comprise many known resilient members, for example a spring 76A, a spring 76B and a spring 76C. In some embodiments, resilient member 74 is positioned between the upper and lower components to provide shock absorption without the springs. In some embodiments, the at least one resilient member is positioned between the upper and lower components without the resilient material. The resilient materials and at least one resilient member may comprise resilient materials and members as described in U.S. application Ser. No. 11/051,513, entitled "Intervertebral Prosthetic Disc with Shock Absorption", filed on Feb. 4, 2005, the full disclosure of which is incorporated herein by reference.

Upper component 70 and lower component 72 are configured to slide relative to one another. Upper component 70 comprises an upper slide structure, for example an inner annular sleeve 82. Lower component 72 comprises a lower slide structure, for example an outer annular sleeve 84. The upper slide structure mates with the lower slide structure, such that the two slide structures permit the upper component to slide relative to the lower component, for example with a telescopic slide mechanism 80.

In some embodiments, the sequential motion of the core parts relative to each other can change the volume chamber 71 so as to provide an inflow and outflow of bodily fluids between the sliding members of the core, such that the fluid flow provides and facilitates lubrication of the sliding members with bodily fluids.

When implanted between vertebrae, at least one of resilient material 74 or the at least one resilient member can resiliently absorb shocks transmitted vertically between upper and lower vertebrae of the patient's spinal column. This shock absorption is related to the material properties and dimensions of the resilient material and resilient members, for example Young's modulus of elasticity. In general, an increased thickness of the resilient material and/or members will increase absorbance of shocks, with more elastic, or springy compression between the vertebrae. In some embodiments, the resilient material may comprise a damping material and/or damping characteristics to improve shock absorption. For example, many resilient materials as described herein also comprise damping materials.

Selected shock absorbing core 16 comprises a height 78 and a width 58 that can be related to the shock absorbing characteristics of the core and/or prosthesis. In many embodiments, the core can absorb shocks to the vertebrae with compression along height 78, such that height 78 can decrease with compression of the core due to forces along the spine. As the thickness of the prosthesis is related to the height of the core, in some embodiments the height of the prosthesis will change with the core, for example decrease when the core is compressed. In many embodiments, the height of the prosthesis corresponds to a distance between serrated and microfinished surfaces 18, 40 of the plates 12, 14 that locate against the opposing vertebrae. In some embodiments, an increase of height 78 can increase shock absorption and resiliency of the core, for example with increased thickness of the shock absorbing materials and/or increased length of the resilient members, for example the resilient members such as compressible resilient springs. In some embodiments, width 58 of the selected core may also affect properties of the endplates.

Referring now to FIG. 1D, a plurality 100 of selectable shock absorbing cores is shown with differing heights and differing resiliencies, according to embodiments of the present invention. Plurality 100 comprises a first core 110A, a second core 110B and a third core 110C.

First core 110A comprises an upper component 116A and a lower component 118A. A resilient material 112A is disposed between upper component 116A and lower component 118A. At least one resilient member 114A extends between upper component 116A and lower component 118A. First core 110A comprises a first height 122A. Resilient material 112A comprises a thickness 124A that corresponds to a length of at least one resilient member 114A. The resilience and shock absorption of first core 110A corresponds to thickness 124A, such that the resilience and shock absorption increase with increasing of thickness of 124A. First core 110A comprises an indicia, for example a marking 120A on the lower component to identify the first core, such that first core 110A can be identified and selected from among plurality 100.

Second core 110B comprises an upper component 116B and a lower component 118B. A resilient material 112B is disposed between upper component 116B and lower component 118B. At least one resilient member 114B extends between upper component 116B and lower component 118B. Second core 110B comprises a second height 122B. Resilient material 112B comprises a thickness 124B that corresponds to a length of at least one resilient member 114B. The resilience and shock absorption of second core 110B corresponds to thickness 124B, such that the resilience and shock absorption increase with increasing thickness of 124B. Second core 110B comprises an indicia, for example a marking 120B on the lower component to identify the second core, such that second core 110B can be identified and selected from among plurality 100.

Third core 110C comprises an upper component 116C and a lower component 118C. A resilient material 112C is disposed between upper component 116C and lower component 118C. At least one resilient member 114C extends between upper component 116C and lower component 118C. Third core 110C comprises a third height 122C. Resilient material 112C comprises a thickness 124C that corresponds to a length of at least one resilient member 114C. The resilience and shock absorption of third core 110C corresponds to thickness 124C, such that the resilience and shock absorption increase with increasing thickness of 124C. Third core 110C comprises an indicia, for example a marking 120C on the lower component to identify the third core, such that third core 110C can be identified and selected from among plurality 100.

In many embodiments, some characteristics first core 110A, second core 110B and third core 110C are substantially the same, such that the cores are interchangeable. For example, a radius of curvature of the upper component of each core may be substantially the same, such that the plates articulate without point contact between the upper curve surface of the upper components. Resilient material 112A, resilient material 112B and resilient material 112C may comprise the substantially the same resilient material, for example an elastomer. In some embodiments, the curved surfaces of the lower components of each core may be substantially the same such that the selected core can slide over the bottom endplate.

In many embodiments, the cores may comprise predetermined characteristics that can be identified by the markings For example, third core 110C may comprise the most resilient core of the plurality with the most shock absorption, while first core 110A may comprise the least resilient core of the plurality with the least shock absorption. Also, third core 110C may comprise the core which provides the largest maximum angle of inclination between the plates of the plurality, while first core 110A may comprise core which provides the smallest angle of inclination between the plates.

In many embodiments, each core of the plurality of core comprises an intended maximum compression under normal patient activity. In some embodiments, first core 110A comprises a maximum compression of ⅓ mm along first height 122A with normal patient activity; second core 110B comprises a maximum compression of ⅔ mm along second height 122B with normal patient activity; and third core 110C comprises a maximum compression of 1 mm along third height 122C with normal patient activity. In some embodiments, the maximum compression can be limited with stops, for example maximum travel of inner sleeve 82 relative to outer sleeve 84 such that inner sleeve 82 on upper component 70 contacts lower core component 72 to limit compression. In some embodiments, the plurality of cores may comprise a substantially incompressible core, for example a core made entirely of metal, such as cobalt chrome. In such embodiments, the range of compression provided by the plurality of cores can be from about 0 mm to about 1 mm. A core with maximum compression of substantially zero may comprises a core made entirely from metal, for example cobalt chrome.

FIG. 1E schematically illustrates a first maximum angle of inclination 108A with the first shock absorbing core of FIG. 1D positioned between an upper endplate 102 and a lower endplate 104. First shock absorbing core 110A comprises first thickness 122A. At maximum angle of inclination 108A, upper plate 102 contacts lower plate 104 at a contact locus 106, for example contact formations as described above. Maximum angle of inclination 108A is determined by thickness 122A.

FIG. 1F schematically illustrates a second maximum angle of inclination 108B with the second shock absorbing core of FIG. 1D positioned between upper endplate 102 and lower endplate 104. Second shock absorbing core 110B comprises second thickness 122B. At maximum angle of inclination 108B, upper plate 102 contacts lower plate 104 at contact locus 106, for example contact formations as described above. Maximum angle of inclination 108B is determined by thickness 122B.

FIG. 1G schematically illustrates a third maximum angle of inclination 108C with the third shock absorbing core of FIG. 1D positioned between upper endplate 102 and lower endplate 104. Third shock absorbing core 110C comprises third thickness 122C. At maximum angle of inclination 108C, upper plate 102 contacts lower plate 104 at contact locus 106, for example contact formations as described above. Maximum angle of inclination 108C is determined by thickness 122C.

In some embodiments, the plurality of cores may comprise a constant height among the cores such that the maximum angle of inclination remains constant, while the shock absorption varies. In such embodiments, the thickness of the resilient material and/or thickness of the at least one resilient member differ among the cores of the plurality, while thicknesses of the upper and lower components differ so as to compensate for the different thicknesses of the resilient material and/or thickness of the at least one resilient member. Thus, the thicknesses of the cores among the plurality remain constant.

Referring now FIG. 1H a plurality 140 of selectable shock absorbing cores of constant height is shown with differing widths and differing resiliencies. Plurality 140 comprises a first core 150A, a second core 150B and a third core 150C.

First core 150A comprises an upper component 156A and a lower component 158A. A resilient material 152A is disposed between upper component 156A and lower component 158A. At least one resilient member 154A extends between upper component 156A and lower component 158A. First core 150A comprises a first height 162A and a first dimension across 166A, for example a diameter. Resilient material 152A comprises a thickness 164A that corresponds to a length of at least one resilient member 154A. The resilience and shock absorption of first core 160A corresponds to thickness 164A, such that the resilience and shock absorption increase with increasing of thickness 164A. First core 150A comprises an indicia, for example a marking 160A on the lower component to identify the first core, such that first core 150A can be identified and selected from among plurality 140.

Second core 150B comprises an upper component 156B and a lower component 158B. A resilient material 152B is disposed between upper component 156B and lower component 158B. At least one resilient member 154B extends between upper component 156B and lower component 158B. Second core 150B comprises a second height 162B and a second dimension across 166B, for example a diameter. Resilient material 152B comprises a thickness 164B that corresponds to a length of at least one resilient member 154B. The resilience and shock absorption of second core 160B corresponds to thickness 164B, such that the resilience and shock absorption increase with increasing of thickness 164B. Second core 150B comprises an indicia, for example a marking 160B on the lower component to identify the second core, such that second core 150B can be identified and selected from among plurality 140.

Third core 150C comprises an upper component 156C and a lower component 158C. A resilient material 152C is disposed between upper component 156C and lower component 158C. At least one resilient member 154C extends between upper component 156C and lower component 158C. Third core 150C comprises a third height 162C and a third dimension across 166C, for example a diameter. Resilient material 152C comprises a thickness 164C that corresponds to a length of at least one resilient member 154C. The resilience and shock absorption of third core 160C corresponds to thickness 164C, such that the resilience and shock absorption increase with increasing of thickness 164C. Third core 150C comprises an indicia, for example a marking 160C on the lower component to identify the second core, such that third core 150C can be identified and selected from among plurality 140.

The height of several cores of the plurality is substantially the same, such that the maximum angle of inclination between the plates is substantially the same for each of the several cores. In some embodiments, first height 162A, second height 162B and third height 162C are substantially the same, such that the maximum angle of inclination of the plates is substantially the same.

The each core of the plurality can be identified in many ways. In some embodiments, the core may comprise an indicia that comprises at least one of a color of the core, a marking on the core, a height of the core or a width of the core. The indicia may be located on the upper component of the core, or the lower component of the core.

The resilient material may comprise many known materials and may comprise at least one resilient material. In some embodiments, the at least one resilient material comprises a polymer. The at least one resilient material may comprise a hydrogel. The at least one resilient support member may be disposed within the resilient material and attached to the upper and lower components comprising the upper and lower curved surfaces.

In many embodiments, the upper and lower components and the curved surfaces formed thereon comprise at least one a polymer, a ceramic or a metal. The metal can comprise at least one of cobalt chrome molybdenum, titanium or stainless steel.

Figure 2:
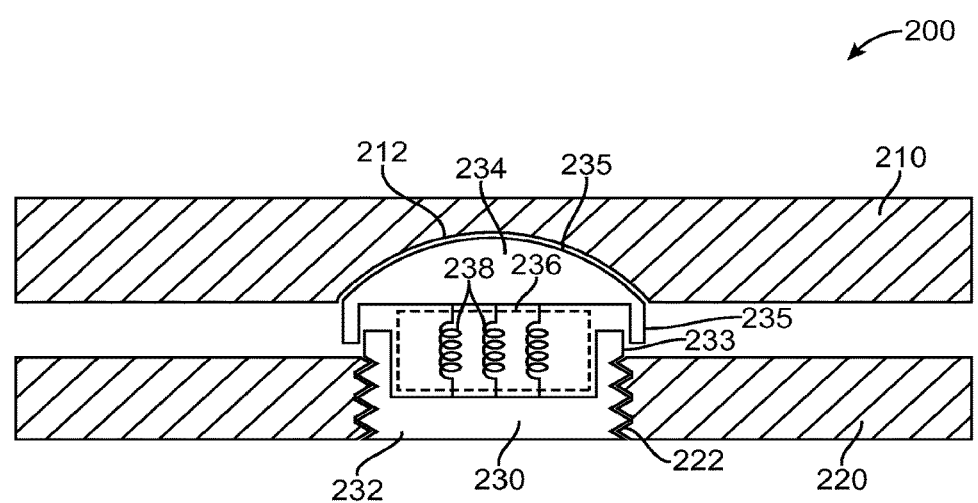
FIG. 2 is a cross-sectional view a prosthetic disc with a selected core attached to a lower plate, according to embodiments of the present invention.

Referring now FIG. 2, a cross-sectional view is shown of a prosthetic disc 200 with a selected shock absorbing core 230 attached to a lower plate 220. Selected shock absorbing core can be selected from a plurality of cores, for example as described above. Prosthetic disc 200 comprises an upper plate 210. Selected shock absorbing core 230 is positioned between the upper plate and the lower plate. Selected shock absorbing core 230 comprises a lower component 232 and an upper component 234. Core 230 comprises a resilient material between upper component 234 and lower component 232. At least one resilient member, for example coils 238 is shown between upper component 234 and lower component 232. Lower component 232 comprises a lower slide structure 233, for example an annular inner sleeve. Upper component 234 comprises an upper slide structure, for example an outer annular sleeve 235. The upper and slide structures comprise a sliding structure, for example a sliding telescopic joint, such that the selected core and resiliently absorb shocks to the prosthesis when positioned in the intervertebral space.

Lower plate 220 can be attached to selected shock absorbing core 230 in many known ways. For example, the selected shock absorbing core can be attached to lower plate by locking the selected core into the lower plate with a detent. Lower plate 220 comprises threads 222 to attach the selected shock absorbing core to the lower plate, for example in the operating room before the prosthesis is inserted into the intervertebral space.

In some embodiments, the shock absorbing core can be inserted between the intervertebral plates after the plates have been inverted into the intervertebral space, as described in U.S. Pat. No. 6,936,071, the full disclosure of which is incorporated herein by reference. The core can be compressed to a low profile configuration when the core is inserted between the plates to minimize distraction of the vertebrae when the core is inserted between the plates. Once the core is locked into position, the core can provide two piece ball and socket motion and shock absorption.

Shock absorbing core 230 comprises and an upper curved spherical surface 235. Upper plate 210 comprises a lower curved spherical surface 212. Upper curved spherical surface 235 and lower curved spherical surface 212 each comprises a radius of curvature. The radius of curvature of the upper curved spherical surface 235 and lower curved spherical surface 212 are substantially the same, such that the upper and lower curved surfaces form a ball and socket joint, as described in U.S. Pat. No. 6,740,118, the full disclosure of which is incorporated by reference. In some embodiments, the selected shock absorbing core comprises and indicia to identify the core, for example a letter etched in upper curved spherical surface 235.

Figure 3:
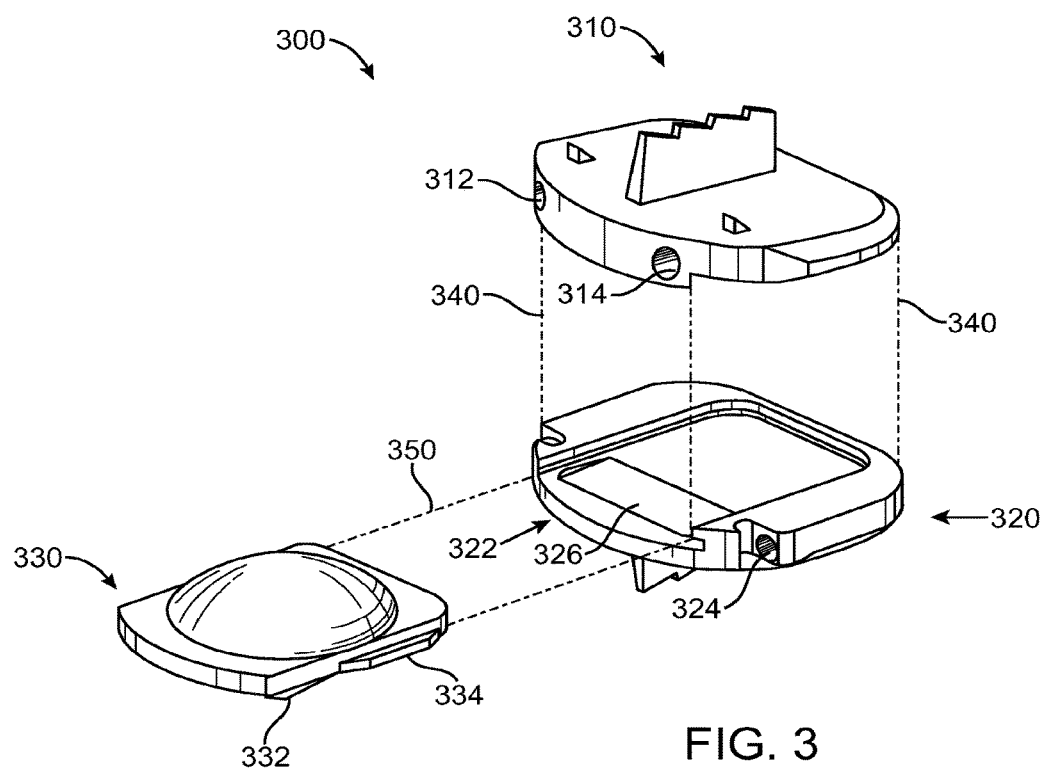
FIG. 3 shows an intervertebral prosthesis with an upper plate, a lower plate, and a selected shock absorbing core that locks into the lower plate to provide ball and socket motion, according to embodiments of the present invention.

FIG. 3 shows an intervertebral prosthesis 300 with an upper plate 310, a lower plate 320, and a selected shock absorbing core 330 that locks into the lower plate to provide ball and socket motion. Selected shock absorbing core 330 comprises a core selected from a plurality of shock absorbing cores as described above. Upper plate 310 comprises a channel 312 and a channel 314, for example as described in U.S. Pat. No. 6,936,071, the full disclosure of which is incorporated by reference. Lower plate 320 comprises a channel 322 sized to receive core 330. Lower plate 320 comprises a channel 324, and an indentation 326. Lower plate 320 may comprise a second channel similar to channel 324 that is disposed on the lower plate equidistant from the middling of the lower plate and opposite the midline. Selected shock absorbing core 330 comprises a flange 334 and a detent 332.

The upper plate 310 and lower plate 320 are sized to nest together when inserted into the intervertebral space, as indicated by lines 340. Once the upper and lower plates are positioned together in the intervertebral space, selected shock absorbing core 330 can be slid between upper plate 310 and lower plate 320 as indicated by lines 350. Channel 322 receives the selected shock absorbing core and flange 334. When the selected shock absorbing core is positioned in the lower plate, detent 332 extends into indentation 326 so as to lock the selected shock absorbing core into position in lower plate 320.

Channel 312, channel 314 and channel 324 are sized to receive prongs of an insertion tool, for example as describe in U.S. Pat. No. 5,314,477, the full disclosure of which is incorporated herein by reference. In some embodiments, the channels on the upper and lower plate receive an instrument that presses the upper and lower plates together so as to compress core 330 and minimize distraction when the core is inserted between the upper and lower plates while the plates are position in the intervertebral space.

Referring now to FIGS. 4A-4E a method is shown for inserting an intervertebral disc prosthesis 404 comprising a selected shock absorbing shock absorbing core 412, according to embodiments of the present invention. Prosthesis 402 is inserted into an intervertebral space IS between two adjacent vertebrae V with a resilient shock absorbing core that can compress during insertion into the disc space so as to minimize distraction. The method involves selecting a shock absorbing core, as described above, and inserting the disc prosthesis 404 partway into the space IS while the prosthesis 404 is constrained (FIG. 4A), for example as described in U.S. application Ser. No. 10/913,780, entitled "Methods and Apparatus for Invertebral Disc Prosthesis Insertion", the full disclosure of which is incorporated herein by reference. To insert the prosthesis 404 partway under constraint, an insertion device 402 may be used. Such an insertion device 402 may suitably include a grasping member 410 coupled with an elongate shaft 408. At an end opposite the grasping member 410 (not shown), the insertion device 402 may include a handle, an actuator to control the grasping member 410 and/or any other suitable features.

The prosthesis 404 may be inserted as far into the intervertebral space IS under constraint as is desired. In some embodiments, for example, the prosthesis 404 is inserted under constraint approximately one-third of the way into the space IS. In other embodiments, the prosthesis 404 may be inserted less than one-third of the way, closer to one-half of the way, or any other suitable distance into the space IS.

Figure 4A:
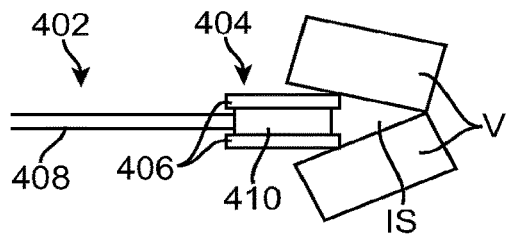
FIGS. 4A-4E show a method of inserting a shock absorbing prosthesis, according to embodiments of the present invention.
Figure 4B:
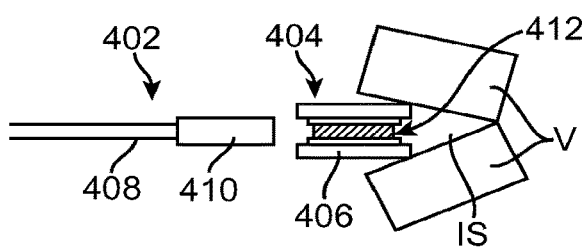

As shown in FIG. 4B, once the prosthesis 404 is inserted partway under constraint, the insertion device 402 may be removed, thus releasing the prosthesis 404 from constraint. From this point forward, the endplates 406 of the prosthesis 404 are free to move about the prosthesis shock absorbing core 412. Examples of such a prosthesis 404 with endplates 406 and selected shock absorbing core 412 are described above.

Figure 4C:
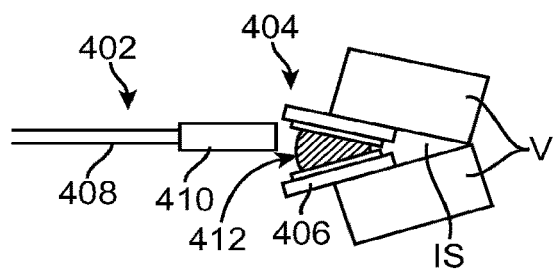
Figure 4D:
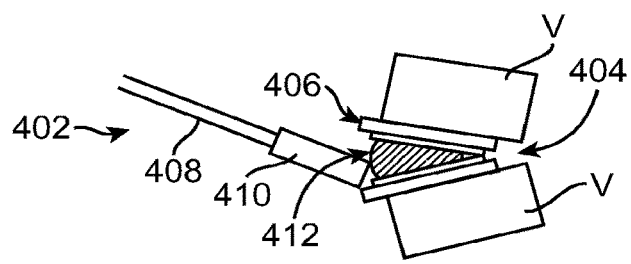
Figure 4E:
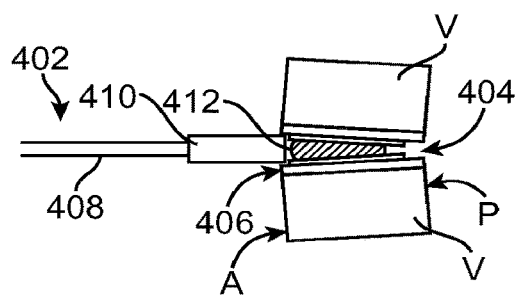

Referring now to FIGS. 4C-4E, in some embodiments the insertion device 402 may be used to push the unconstrained prosthesis 404 farther into the intervertebral space. In some embodiments, one or more separate pusher devices may be used in addition to or instead of the insertion device 402 for pushing the prosthesis 104 farther into the space IS. FIGS. 4C and 4D show that the grasping member 410 of the insertion device 402 can be adapted to push individually against the upper (FIG. 4C) and lower (FIG. 4D) endplates 406. As shown in FIG. 4E, the grasping member 410 may also be adapted to push simultaneously against the upper and lower endplates 406, thus pushing the prosthesis 404 as a unit farther into the intervertebral space IS.

By inserting the prosthesis 404 farther into the space IS while it is unconstrained and compressing the shock absorbing core, thus allowing the endplates 406 to articulate about the shock absorbing core 412 and come closer together, the method reduces the need for increasing the height of the intervertebral space IS with distraction of the vertebrae V away from each other. Because the endplates 406 are free to articulate and can compress the shock absorbing core 416 to move the plates together, the prosthesis 404 is better able to conform to the intervertebral space IS, thus reducing trauma to the vertebrae V and also limiting trauma to surrounding structures caused by over-distraction.

The unconstrained prosthesis 404 may be inserted as far into the intervertebral space IS as is desired. In some embodiments, for example, the prosthesis 404 is pushed far enough into the space IS so that a center of rotation of the prosthesis 404 is closer to a posterior edge P (FIG. 4E) of the vertebrae V than to an anterior edge A of the vertebrae V. In alternative embodiments, any other suitable insertion distance or depth may be used. Once a desired amount of insertion is achieved, the insertion device 402 is removed and the prosthesis 404 is in place between the two adjacent vertebrae V.

In various embodiments, the method just described may include fewer steps or additional steps. For example, in one embodiment, a spreader device is inserted between the two vertebrae V to spread them apart before inserting the constrained prosthesis 404. An example of such a spacing device is described in PCT Patent Application No. 2004/000171, the full disclosure of which is incorporated by reference. In such embodiments, the insertion device 402 can be sized to fit between opposing jaws of the spreader device, such that the jaws can compress the shock absorbing core so as to minimize distraction. When the prosthesis 404 is partially inserted, the spreader device is removed from the intervertebral space IS, and the prosthesis 404 is released from constraint and inserted the rest of the way into the space IS. Also in some embodiments, a midline indicator device may be used to facilitate the location of a midline on one or both of the two adjacent vertebrae V. An example of such a midline indicator device is described in PCT Patent Application No. 2004/000170, the full disclosure of which is incorporated herein by reference. In some embodiments, the midline indicator can be used before the disc prosthesis 404 is inserted. These and other steps or features may be included in various embodiments of the method without departing from the scope of the invention.

Figure 5:
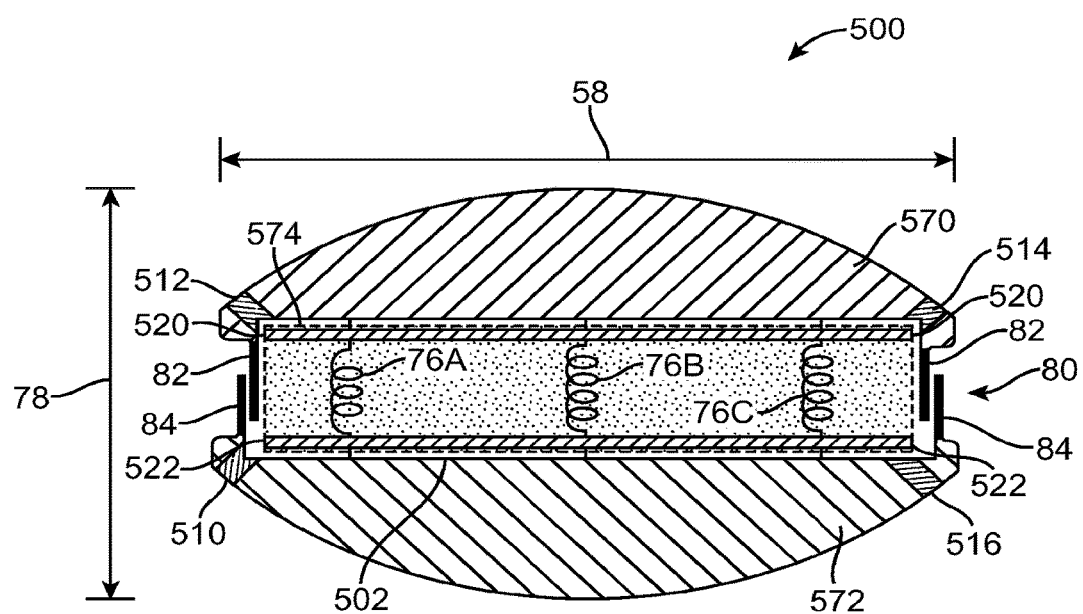
FIG. 5 shows a shock absorbing core with channels to allow fluid to move through the core, according to embodiments of the present invention.

FIG. 5 shows a shock absorbing core 500 with channels to allow fluid to move through the core, according to embodiments of the present invention. Many components of core 500 are similar to core 16 shown above. Core 500 comprises a channel 510, a channel 512, a channel 514 and a channel 516. An upper component 570 and lower component 572 of core 500 define a chamber 502. Resilient material 574 and resilient member 76A, resilient member 76B and resilient member 76C can be disposed between the upper and lower components within chamber 502. Resilient material 574 may comprise an upper channel 520 and a lower channel 522 to permit drainage from resilient material 574 and/or the chamber. In many, embodiments, core 500 comprises channel 510, channel 512, channel 514 and channel 516 without resilient material 574. Channel 510, channel 512, channel 514 and channel 516 extend from chamber 502 to an external surface of core 500 to permit fluid to drain from the core and/or pass through the core.

The channels in the upper and lower components and resilient material in core 500 permit fluid to pass through the core while the patient is stationary and can pump fluid through the core during patient activity. Work in relation to embodiments of the present invention suggests that static accumulation of bodily fluids in the core may occur. By passing fluid through the core, bacteria build up due to static enclosed fluids may be avoided. When upper component 570 moves toward lower component 572 a volume of chamber 502 decreases so as to drive fluid, for example bodily fluid from chamber 502. When the upper component 520 moves away from lower component 572, the volume of chamber 502 increases so as to draw fluid into the chamber. As an active person will resiliently compress and expand core 500 with activity, core 500 can pump fluid in and out of the core by moving the upper and lower components toward and away from each other with patient movement. In many embodiments, the channels are large enough to enable fluid flow, and small enough to inhibit tissue in growth that may compromise the shock absorbing motion of the core. The number of channels in the upper and lower components and/or resilient material can be selected so as to enable fluid flow and not weaken the core structures.

FIGS. 6A to 6D show a placement instrument 600 capable of compressing the core when the implant is inserted into the intervertebral space, according to embodiments of the present invention. The placement instrument can be inserted posteriorly through the canal and/or foramen so as to engage the boney endplates near the disc space, as described in U.S. application Ser. No. 11/787,110, entitled "Posterior Spinal Device and Method", filed Apr. 12, 2007, the full disclosure of which has previously been incorporated herein by reference. In many embodiments, the placement instrument is inserted after two minimally invasive Wiltse incisions and/or dissections and a discectomy that uses a posterior parallel distractor. Placement instrument 600 comprises a distractor with a distractor tip 630 that can be inserted at least partially into the intervertebral space. Instrument 600 comprises a stop to limit penetration of distractor tip 630. Instrument 600 comprises handles 610 to distract the adjacent vertebrae. Instrument 600 comprises a hinge 620 that opens distractor tip 630 upon inward motion of handles 610.

Instrument 600 comprises a compression spring 615 that presses handles 610 apart, so as to oppose inward motion of the handles. By forcing handles 610 apart, compression spring 615 can close distractor tip 630 so as to compress the core to a narrow profile configuration.

Instrument 600 is adapted to pass the prostheses in an elongate narrow profile configuration into the intervertebral space. Distractor tip 630 comprises a channel 640 with grooves 642 formed therein. Channel 640 is dimensioned to pass the prosthesis in an elongate narrow profile configuration. Grooves 642 are dimensioned and spaced to receive anchors on the external surfaces of the support components, for example pyramidal components as described above. In some embodiments, the anchors may comprise elongate pyramidal anchors and or elongate keels or flanges and the grooves adapted to pass the elongate anchors with the groove aligned with the elongate anchor. In many embodiments, channel 640 is sized to distract the vertebrae with distractor tip 630 while the elongate prosthesis slides down channel 640. Near hinge 620, channel 640 can be sized to pass the prosthesis with a sliding fit.

Instrument 600 comprises an insertion tool 650 to advance the prosthesis along channel 640 so as to advance the prosthesis into the intervertebral space. Insertion tool 650 comprises a shaft 654 and a handle 652. Handle 652 is connected to shaft 654. In many embodiments handle 652 comprises a grub screw, and handle 652 and shaft 654 comprise strong materials such that handle 652 can be hammered so as to drive the prosthesis distally into the intervertebral space and distract the vertebrae with separation of distal tip 630. Compression spring 1651 can expand to force handles 610 open and close distractor tip 630 so as to press the upper and lower supports of the prosthesis together and compress the selected shock absorbing core. This compression of the shock absorbing core can reduce the height of the prosthesis and reduce distraction of the intervertebral space and/or surrounding tissues when the implant is inserted into the intervertebral space.

The selectable shock absorbing cores and insertion tool may comprise a system for narrow profile insertion of the prosthesis into the intervertebral space so as to minimize distraction. The compression spring can compress the shock absorbing prosthesis to a narrow profile configuration. Although a compression spring is shown, many springs and/or resilient members and/or materials can be used to compress the prosthesis to a narrow profile configuration, for example resilient materials and members similar to those used in the core as described above. In many embodiments, the selected core provides maximum compression within a range from about ⅓ mm to about 1 mm during patient activity, and the narrow profile configuration of the core comprises a maximum compression of the core, for example ⅓ mm, ⅔ mm or 1 mm, depending on the core as described above. In many embodiments, an expanded configuration of the core comprises an unloaded configuration of the core. In many embodiments, the resilient member and/or material is connected to the distractor tips so as to compress the selected shock absorbing prosthesis and/or core to the narrow profile configuration, for example with maximum compression of the core as described above, when the core is positioned in the channel for insertion into the patient.

Figure 7A:
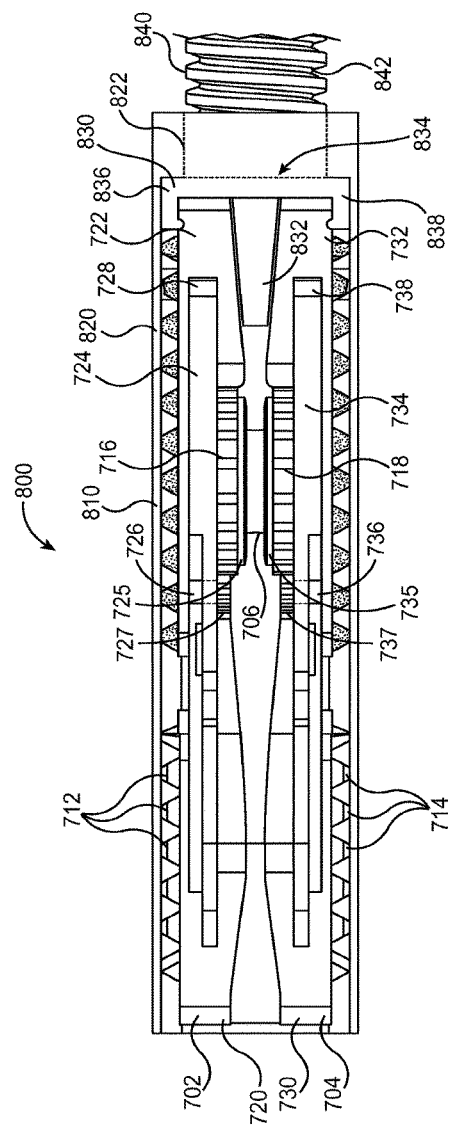
FIGS. 7A and 7B schematically illustrate details of the self-expanding intervertebral joint assembly loaded in a cartridge, in accordance with embodiments of the present invention.
Figure 7B:
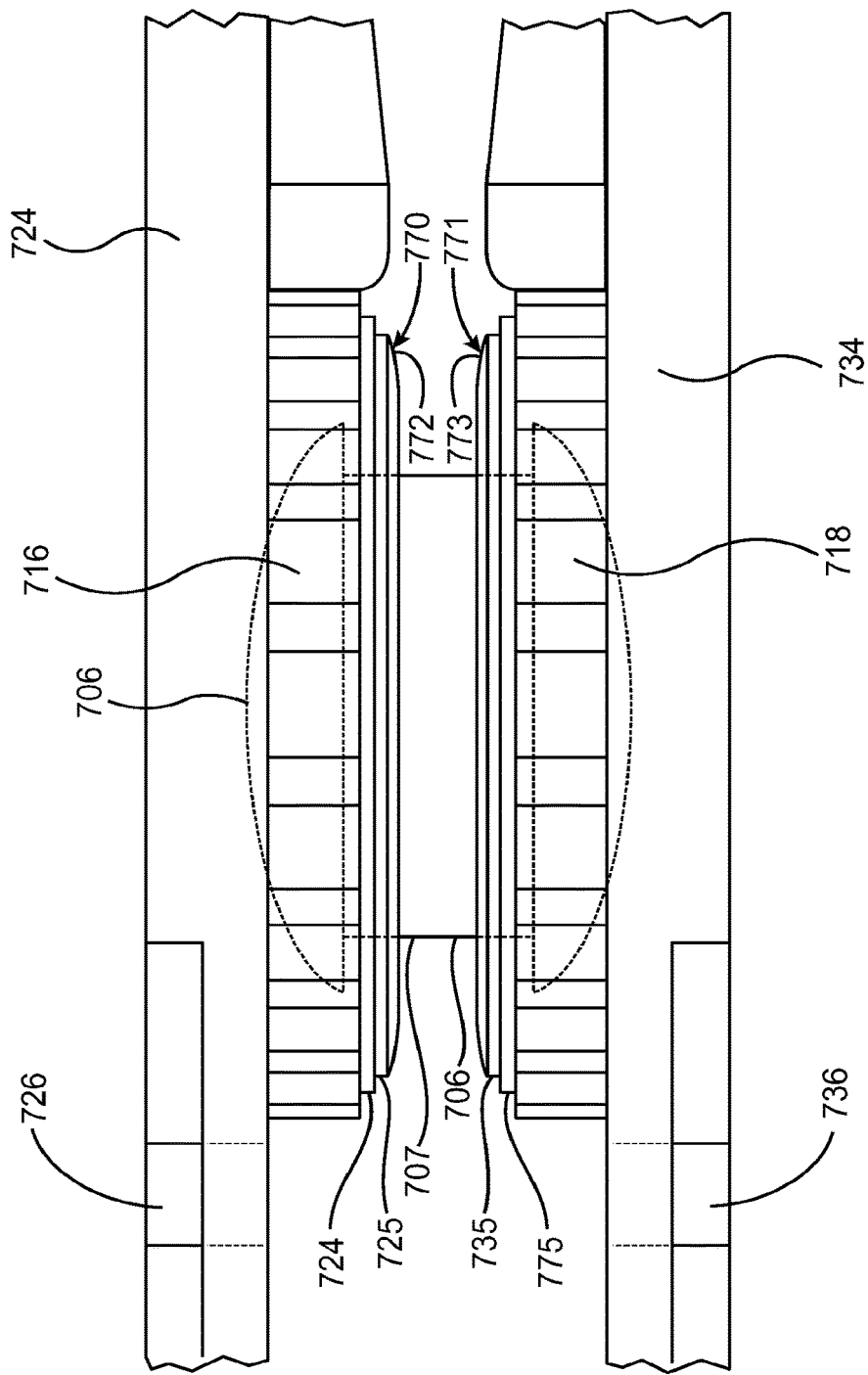

FIGS. 7A and 7B schematically illustrate a selectable shock absorbing core and details of a self-expanding intervertebral joint assembly loaded in a cartridge as described in U.S. application Ser. No. 11/787,110, entitled "Posterior Spinal Device and Method", filed Apr. 12, 2007, the full disclosure of which has previously been incorporated herein by reference. A system comprising shock absorbing cores, as described above, can be provided to the physician. The physician can select the core from among a plurality of cores as described above.

Outer cartridge casing 820 extends over at least a portion of intervertebral joint assembly to permit advancement of the joint assembly into at least a portion of the intervertebral space while the joint assembly is substantially covered with outer cartridge casing 820. Outer cartridge casing 820 covers pyramidal anchors 712 and pyramidal anchors 714. Distal component 720 of upper support 702 and distal component 730 of lower support 704 are located near an opening in outer cartridge casing 820. Inner cartridge part 830 includes a wedge 832, upper flange 836 and lower flange 838. The upper and lower flanges include inner opposing surfaces, and the inner surface of each flange opposes one of the wedge surfaces to clamp the components of the upper and lower supports in a parallel configuration Inner cartridge part 830 is connected to shaft 840.

Self expanding intervertebral joint assembly 700 includes structures to permit articulation between upper support 702 and lower support 704 to restore motion between the vertebrae. Upper support 702 has a protruding structure 725 which extends from middle component 724 and has a concave surface feature formed therein, as shown herein above, which mates the upper surface of shock absorbing biconvex core 706. Lower support 704 has a protruding structure 735 which extends from middle component 734 and has a concave surface feature formed therein, which mates the lower surface of shock absorbing biconvex core 706. In an alternate embodiment, the features of the upper and lower support are in direct contact and mate to provide articulation. For example, the upper support can have a protrusion with a convex surface, and the lower support can have a protrusion with a concave surface, in which the two surfaces mate to form a load bearing articulate joint.

Protruding structure 725 and protruding structure 726 can also include structures to retain the shock absorbing biconvex core and upper and lower retention ring gears, respectively. In many embodiments, shock absorbing core 607 comprises an annular channel 707 around the periphery of the shock absorbing core Annular channel 707 is sized to receive retention ring structures of the upper and lower plates, so as to retain the shock absorbing core between the plates.

Protruding structure 725 can include a retention ring, rim or annular flange as described above such as an annular flange 770 that projects radially inward toward shock absorbing biconvex core 706 to retain shock absorbing biconvex core 706. Protruding structure 735 can include a radially inwardly projecting retention ring, rim or annular flange such as an annular flange 771 that extends toward shock absorbing biconvex core 706 to retain shock absorbing biconvex core 706. Annular flange 770 has a bevel 772 formed thereon to limit motion between the upper and lower supports. Annular flange 771 has a bevel 773 formed thereon to limit motion between the upper and lower supports. Bevel 772 and bevel 773 can be inclined so as to avoid point loading when the upper and lower supports are a the maximum angle of inclination. Annular flange 770 and annular flange 771 can extend into annular channel 701 to retain the core. In some embodiments, the plates as described above include an upper retention ring and a lower retention ring with each of the upper and lower retention rings shaped to engage an annular channel of the core so as to retain the core between the plates.

Retention ring gear 716 can have an annular shape formed to mate with protruding structure 725. Protruding structure 725 can include an outer circular surface that mates with an inner surface of inner annular surface of retention ring gear 716. Retention ring gear 716 can rotate around protruding structure 725. In addition to inwardly protruding annular flange 770 that retains shock absorbing biconvex core 706, protruding structure 725 can include a retention element 775 such as an outwardly protruding annular flange and/or C-ring clip to retain retention ring gear 716.

Retention ring gear 718 can also have an annular shape formed to mate with protruding structure 735. Protruding structure 735 can include an outer circular surface that mates with an inner annular surface of retention ring gear 718. Retention ring gear 718 can rotate around protruding structure 735. In addition to an inwardly protruding annular flange that retains shock absorbing biconvex core 706, protruding structure 735 can include an outwardly protruding retention element 775 such as an annular flange and/or C-ring clip to retain retention ring gear 718.

Implant 700 can include structures that pivot while the upper and lower supports are formed. A pivot gear 727 can engage upper retention ring gear 716. Pivot gear 727 is connected to joint 726 so that rotation of pivot gear 727 rotates pivot joint 726 to rotate distal component 720. A pivot joint 728 connects proximal component 722 to middle component 724 of upper support 702. Rotation about pivot joint 728 pivots middle component 724 toward the deployed position. A pivot gear 737 can engage lower retention ring gear 718. Pivot gear 737 is connected to pivot joint 736 so that rotation of pivot gear 737 rotates pivot joint 736 to rotate distal component 704 toward the deployed position. A pivot joint 738 connects proximal component 732 to middle component 734 of lower support 704. Rotation about pivot joint 738 pivots middle component 734 toward the deployed position.

Wedge 832, upper flange 836 and lower flange 838 restrain motion of the joint assembly during deployment by clamping the joint assembly while the joint assembly is advanced. Wedge 832 is positioned between upper support 702 and lower support 704. Wedge 832 and upper flange 836 engage proximal component 722 of upper support 702. Wedge 832 and lower flange 838 engage proximal component 732 of lower support 704. Inwardly facing projections are provided on the ends of the upper flange 836 and lower flange 838. Advancement of inner cartridge part 830 advances wedge 832, upper, the upper and lower supports distally to engage gears of the support.

In many embodiments, the shock absorbing core can be compressed with an instrument during insertion to allow for a lower profile during insertion. For example, casing 810 of cartridge 800 can be sized to compress the core during insertion so as to lower the profile of the core. The core can also be compressed during insertion through a tube, sleeve, or the like such that core assumes a low profile compressed configuration during insertion so as to minimize the invasiveness of the procedure, for example with a posterior lateral Wiltse approach as described in U.S. application Ser. No. 11/787,110, entitled "Posterior Spinal Device and Method", filed Apr. 12, 2007, the full disclosure of which has previously been incorporated herein by reference. In some embodiments, the core and/or prosthesis can be compressed with forceps while inserted into the intervertebral space.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:
1. An intervertebral disc prosthesis system comprising:
   a disc prosthesis comprising:
      upper and lower supports each support comprising, an outer surface which engages a vertebra and an inner surface; and
      a core configured to be received between the inner surfaces of the upper and lower supports and to slide over the inner surfaces of the upper and lower supports to provide articulation of the intervertebral disc; and a retaining formation which holds the core captive between the upper and lower supports; and wherein the upper and lower supports are adapted to articulate with respect to one another and the core when the core is positioned between the upper and lower supports;

wherein the disc prosthesis is loaded on a cartridge comprising:

a central member configured to be positioned between the inner surfaces of the upper and lower supports; and upper and lower flanges configured to engage the outer surfaces of the upper and lower supports, wherein the central member, upper and lower flanges together clamp the upper and lower supports while the disc prosthesis is advanced.

2. The system of claim 1, wherein the retaining formation includes two or more groove-like recesses spaced apart about a periphery of the core and two or more inwardly directed pegs or pins on one of the upper and lower plates, wherein each peg or pin opposes a spaced recess.

3. The system of claim 2, wherein the spaced recesses are formed in the lateral surfaces of the core.

4. The system of claim 3, wherein the spaced recesses extend radially inward from the lateral surfaces of the core.

5. The system of claim 2, wherein the retaining formation allows anterior, posterior and lateral motion of the core with respect to the first and second plates.

6. The system of claim 2, wherein the pegs or pins are configured to extend into the recesses during sliding motion of the plates over the core.

7. The system of claim 1, wherein the cartridge comprises inwardly facing projections provided on ends of the upper flange and lower flange.

* * * * *